(12) United States Patent
Bouma et al.

(10) Patent No.: US 7,864,822 B2
(45) Date of Patent: Jan. 4, 2011

(54) PROCESS AND APPARATUS FOR A WAVELENGTH TUNING SOURCE

(75) Inventors: Brett Eugene Bouma, Quincy, MA (US); Seok-Hyun (Andy) Yun, Cambridge, MA (US); Wang-Yuhl (William) Oh, Cambridge, MA (US); Johannes F. De Boer, Amstelveen (NL); Guillermo J. Tearney, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 12/369,556

(22) Filed: Feb. 11, 2009

(65) Prior Publication Data

US 2009/0257461 A1 Oct. 15, 2009

Related U.S. Application Data

(62) Division of application No. 11/867,953, filed on Apr. 11, 2008, now Pat. No. 7,724,786, which is a division of application No. 10/861,179, filed on Jun. 4, 2004, now Pat. No. 7,519,096.

(60) Provisional application No. 60/476,600, filed on Jun. 6, 2003, provisional application No. 60/514,769, filed on Oct. 27, 2003.

(51) Int. Cl.
*H01S 3/10* (2006.01)
(52) U.S. Cl. .............................. 372/20; 372/28; 372/32
(58) Field of Classification Search ............... 372/20, 372/28
See application file for complete search history.

(56) References Cited

U.S. PATENT DOCUMENTS

| 4,639,999 A | 2/1987 | Daniele |
| 4,763,977 A | 8/1988 | Kawasaki et al. |
| 4,940,328 A | 7/1990 | Hartman |
| 4,984,888 A | 1/1991 | Tobias et al. |
| 5,202,931 A | 4/1993 | Bacus et al. |
| 5,251,009 A | 10/1993 | Bruno |
| 5,281,811 A | 1/1994 | Lewis |

(Continued)

FOREIGN PATENT DOCUMENTS

| CN | 1550203 | 12/2004 |
| JP | 20030035659 | 2/2003 |
| WO | 2005082225 | 9/2005 |

OTHER PUBLICATIONS

Office Action dated Jul. 7, 2010 for U.S. Appl. No. 11/624,277.
Montag Ethan D., "Parts of the Eye" online textbook for JIMG 774: Vision & Psycophysics, download on Jun. 23, 2010 from http://www.cis.rit.edu/people/faculty/montag/vandplite/pp./chap_8/ch8p3.html.
Office Action dated Jul. 16, 2010 for U.S. Appl. No. 11/445,990.
Office Action dated Jul. 20, 2010 for U.S. Appl. No. 11/625, 135.
Office Action dated Aug. 5, 2010 for U.S. Appl. No. 11/623,852.

(Continued)

*Primary Examiner*—Dung T Nguyen
(74) *Attorney, Agent, or Firm*—Dorsey & Whitney LLP

(57) ABSTRACT

An apparatus and source arrangement for filtering an electromagnetic radiation can be provided which may include at least one spectral separating arrangement configured to physically separate one or more components of the electromagnetic radiation based on a frequency of the electromagnetic radiation. The apparatus and source arrangement may also have at least one continuously rotating optical arrangement which is configured to receive at least one signal that is associated with the one or more components. Further, the apparatus and source arrangement can include at least one beam selecting arrangement configured to receive the signal.

6 Claims, 16 Drawing Sheets

U.S. PATENT DOCUMENTS

| | | | |
|---|---|---|---|
| 5,404,415 | A | 4/1995 | Mori et al. |
| 5,424,827 | A | 6/1995 | Horwitz et al. |
| 5,522,004 | A | 5/1996 | Djupsjobacka et al. |
| 5,565,983 | A | 10/1996 | Barnard et al. |
| 5,801,831 | A | 9/1998 | Sargoytchev et al. |
| 5,836,877 | A | 11/1998 | Zavislan et al. |
| 5,994,690 | A | 11/1999 | Kulkarni et al. |
| 6,007,996 | A | 12/1999 | McNamara et al. |
| 6,010,449 | A | 1/2000 | Selmon et al. |
| 6,078,047 | A * | 6/2000 | Mittleman et al. ....... 250/338.1 |
| 6,107,048 | A | 8/2000 | Goldenring et al. |
| 6,249,630 | B1 | 6/2001 | Stock et al. |
| 6,301,048 | B1 | 10/2001 | Cao et al |
| 6,437,867 | B2 | 8/2002 | Zeylikovich et al. |
| 6,441,892 | B2 | 8/2002 | Xiao et al. |
| 6,441,959 | B1 | 8/2002 | Yang et al. |
| 6,485,413 | B1 | 11/2002 | Boppart et al. |
| 6,593,101 | B2 | 7/2003 | Richards-Kortum et al. |
| 6,611,833 | B1 | 8/2003 | Johnson et al. |
| 6,654,127 | B2 | 11/2003 | Everett et al. |
| 6,657,730 | B2 | 12/2003 | Pfau et al. |
| 6,692,430 | B2 | 2/2004 | Adler |
| 6,900,899 | B2 | 5/2005 | Nevis |
| 6,961,123 | B1 | 11/2005 | Wang et al. |
| 6,996,549 | B2 | 2/2006 | Zhang et al. |
| 7,027,633 | B2 | 4/2006 | Foran et al. |
| 7,072,047 | B2 | 7/2006 | Westphal et al. |
| 7,075,658 | B2 | 7/2006 | Izatt et al. |
| 7,113,288 | B2 | 9/2006 | Fercher |
| 7,113,625 | B2 | 9/2006 | Watson et al. |
| 7,139,598 | B2 | 11/2006 | Hull et al. |
| 7,177,027 | B2 | 2/2007 | Hirasawa et al. |
| 7,272,252 | B2 | 9/2007 | De La Torre-Bueno et al. |
| 7,342,659 | B2 | 3/2008 | Horn et al. |
| 7,458,683 | B2 | 12/2008 | Chernyak et al. |
| 7,530,948 | B2 | 5/2009 | Seibel et al. |
| 7,646,905 | B2 | 1/2010 | Guittet et al. |
| 7,664,300 | B2 | 2/2010 | Lange et al. |
| 7,782,464 | B2 | 8/2010 | Mujat et al. |
| 2002/0024015 | A1 | 2/2002 | Hoffmann et al. |
| 2002/0086347 | A1 | 7/2002 | Johnson et al. |
| 2002/0122182 | A1 | 9/2002 | Everett et al. |
| 2003/0013973 | A1 | 1/2003 | Georgakoudi et al. |
| 2003/0053673 | A1 | 3/2003 | Dewaele et al. |
| 2003/0067607 | A1 | 4/2003 | Wolleschensky et al. |
| 2003/0165263 | A1 | 9/2003 | Hamer et al. |
| 2003/0174339 | A1 | 9/2003 | Feldchtein et al. |
| 2004/0076940 | A1 | 4/2004 | Alexander et al. |
| 2004/0126048 | A1 | 7/2004 | Dave et al. |
| 2004/0126120 | A1 | 7/2004 | Cohen et al. |
| 2004/0189999 | A1 | 9/2004 | De Groot et al. |
| 2004/0239938 | A1 | 12/2004 | Izatt |
| 2004/0246583 | A1 | 12/2004 | Mueller et al. |
| 2005/0036150 | A1 | 2/2005 | Izatt et al. |
| 2005/0059894 | A1 | 3/2005 | Zeng et al. |
| 2005/0065421 | A1 | 3/2005 | Burckhardt et al. |
| 2005/0128488 | A1 | 6/2005 | Milen et al. |
| 2006/0033923 | A1 | 2/2006 | Hirasawa et al. |
| 2006/0164639 | A1 | 7/2006 | Horn et al. |
| 2006/0171503 | A1 | 8/2006 | O'Hara et al. |
| 2007/0038040 | A1 | 2/2007 | Cense et al. |
| 2007/0086017 | A1 | 4/2007 | Buckland et al. |
| 2007/0188855 | A1 | 8/2007 | Milen et al. |
| 2007/0236700 | A1 | 10/2007 | Yun et al. |
| 2007/0258094 | A1 | 11/2007 | Izatt et al. |
| 2008/0007734 | A1 | 1/2008 | Park et al. |
| 2008/0097225 | A1 | 4/2008 | Milen et al. |
| 2008/0204762 | A1 | 8/2008 | Izatt et al. |
| 2009/0273777 | A1 | 11/2009 | Yun et al. |
| 2010/0086251 | A1 | 4/2010 | Xu et al. |
| 2010/0150467 | A1 | 6/2010 | Zhao et al. |

FOREIGN PATENT DOCUMENTS

| | | |
|---|---|---|
| JP | 20040056907 | 2/1992 |

OTHER PUBLICATIONS

Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol, 45, pp. 798-803.
O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical Coherence Tomography of the Human Gastrointestinal Tract-Toward Optical Biopsy," Encoscopy, vol. 32, No. 10, pp. 743-749.
E. Montgomery et al., "Reproducibility of the Diagnosis of Dysplasia in Barrett Esophagus: a Reaffirmation," Apr. 2001, Human Pathology, vol. 32, No. 4, pp. 368-378.
H. Geddert et al., "Expression of Cyclin B1 in the Metaplasia-Dysphasia -Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.
Seltzer et al., (1991) "160 nm Continuous Tuning of a MQW Laser in an External Cavity Across the Entire 1.3 μm Communications Window," Electronics Letters, vol. 27, pp. 95-96.
Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.

* cited by examiner

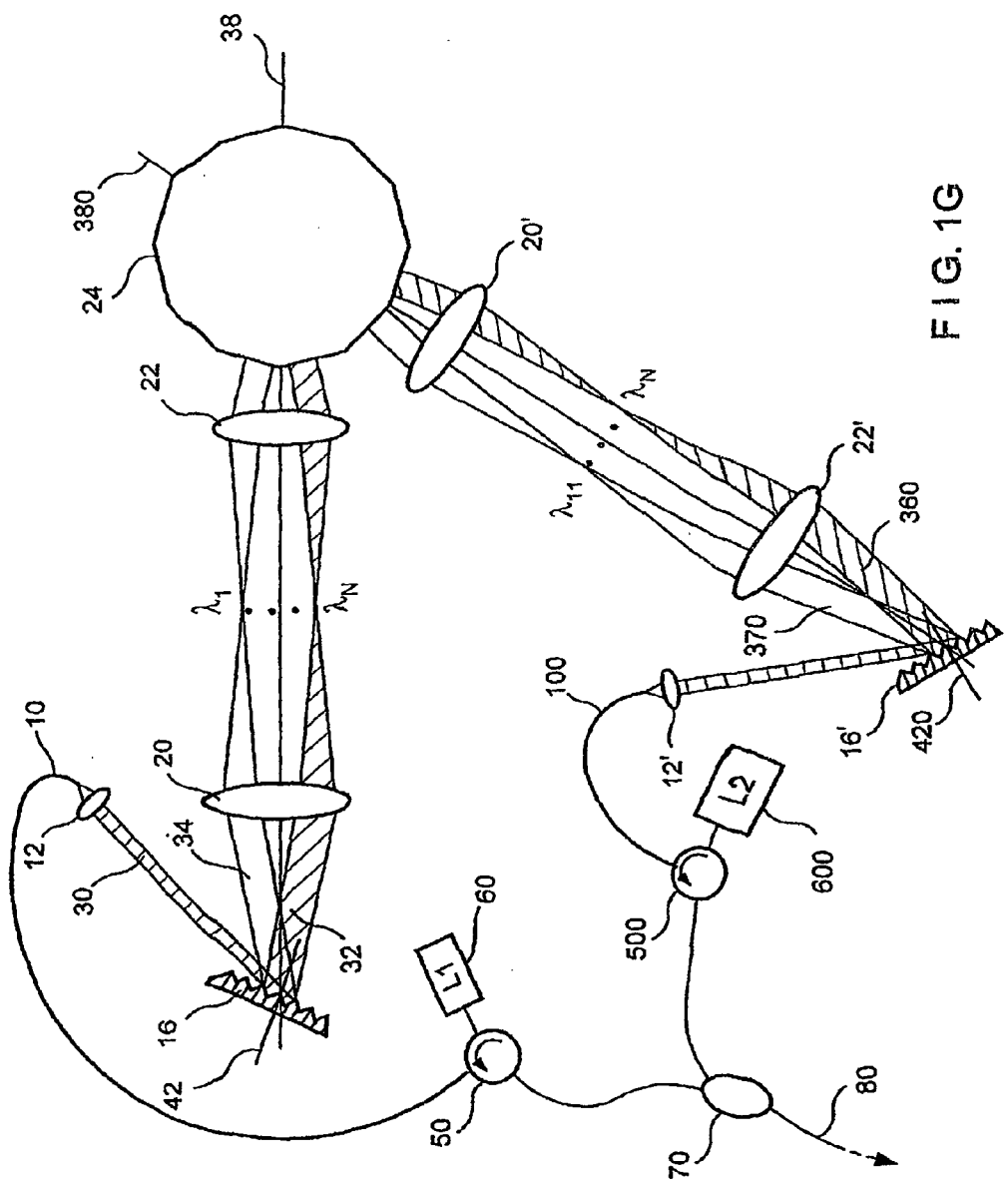

PROCESS AND APPARATUS FOR A WAVELENGTH TUNING SOURCE

CROSS-REFERENCE TO RELATED APPLICATIONS

The present application is a divisional of U.S. patent application Ser. No. 11/867,953 filed Apr. 11, 2008 now U.S. Pat. No. 7,724,786, which is a divisional of U.S. patent application Ser. No. 10/861,179 filed Jun. 4, 2004 now U.S. Pat. No. 7,519,096. This application also claims priority from U.S. Patent Application Ser. No. 60/476,600 filed on Jun. 6, 2003 and U.S. Patent Application Ser. No. 60/514,769 filed on Oct. 27, 2003, the entire disclosures of which is incorporated herein by reference.

FIELD OF THE INVENTION

The present invention relates generally to optical systems and more particularly to an optical wavelength filter system for wavelength tuning.

BACKGROUND OF THE INVENTION

Considerable effort has been devoted for developing rapidly and widely tunable wavelength laser sources for optical reflectometry, biomedical imaging, sensor interrogation, and tests and measurements. A narrow line width, wide-range and rapid tuning have been obtained by the use of an intra-cavity narrow band wavelength scanning filter. Mode-hopping-free, single-frequency operation has been demonstrated in an extended-cavity semiconductor laser by using a diffraction grating filter design. Obtaining single-frequency laser operation and ensuring mode-hop-free tuning, however, may use a complicated mechanical apparatus and limit the maximum tuning speed. One of the fastest tuning speeds demonstrated so far has been limited less than 100 nm/s. In certain applications such as biomedical imaging, multiple-longitudinal mode operation, corresponding to an instantaneous line width as large or great than 10 GHz, may be sufficient. Such width may provide a ranging depth of a few millimeters in tissues in optical coherence tomography and a micrometer-level transverse resolution in spectrally-encoded confocal microscopy.

A line width on the order of 10 GHz is readily achievable with the use of an intra-cavity tuning element (such as an acousto-optic filter, Fabry-Perot filter, and galvanometer-driven diffraction grating filter). However, the sweep frequency previously demonstrated has been less than 1 kHz limited by finite tuning speeds of the filters. Higher-speed tuning with a repetition rate greater than 15 kHz may be needed for video-rate (>30 frames/s), high-resolution optical imaging in biomedical applications.

Accordingly, there is a need to overcome the above-described deficiencies.

SUMMARY OF THE INVENTION

According to the exemplary concepts of the present invention, an optical wavelength filter may be provided that can be tuned with a repetition rate of greater than 15 kHz over a wide spectral range. In addition, a wavelength tuning source comprising such optical filter in combination with a laser gain medium may be provided. The tuning source may be useful in video-rate optical imaging applications, such as the optical coherence tomography and spectrally encoded confocal microscope.

In general, the optical filter according to one exemplary embodiment of the present invention may include a diffraction grating, a rotating polygon scanner, and a telescope. Such optical filter can be operated at a tuning speed more than an order of magnitude higher than the conventional filters. The wavelength tunable light source may be implemented by employing the filter, e.g., in combination with a laser gain medium. The filter and gain medium may further, be incorporated into a laser cavity. For example, a laser can emit a narrow band spectrum with its center wavelength being swept over a broad wavelength range at a high repetition rate.

In one exemplary embodiment of the present invention, an apparatus is provided which includes an arrangement for emitting an electromagnetic radiation that has a spectrum whose mean frequency changes substantially continuously over time. Such radiation is may be associated with a tuning speed that is greater than 100 terahertz per millisecond. The mean frequency can change repeatedly at a repetition rate that is greater than 5 kilohertz or over a range greater than 10 terahertz. The spectrum may have a tuning range covering a portion of the visible, near-infrared or infrared wavelengths. Exemplary spectra may be centered at approximately at 850 nm, 1300 nm or 1700 nm wavelengths. Further, the spectrum may have an instantaneous line width that is smaller than 100 gigahertz. The apparatus may also include a laser cavity with a roundtrip length shorter than 5 m. The apparatus may also have a polygon scanner arrangement which may be adapted to receive at least a portion of the emitted electromagnetic radiation and reflect or deflect the portion to a further location. In addition, a beam separating arrangement can be provided which selectively receives components of the electromagnetic radiation.

According to another exemplary embodiment of the present invention the apparatus for filtering an electromagnetic radiation can include at least one spectral separating arrangement configured to physically separate one or more components of the electromagnetic radiation based on a frequency of the electromagnetic radiation. The apparatus may also have at least one continuously rotating optical arrangement that is configured to receive the physically separated components and selectively direct individual components to a beam selecting arrangement.

In one exemplary variation of the present invention, the spectral separating arrangement includes a diffraction grating, a prism, a grism, an acousto-optic beam deflector, a virtual phased array, and/or an arrayed waveguide grating. The continuously rotating optical arrangement may be a polygon mirror, a diffractive element, a substantially opaque disk having an array of substantially transparent regions, and/or a substantially transparent disk having an array of substantially reflective regions. The spectral separating arrangement may also include a holographic grating mounted on a substrate comprising a continuously rotating optical arrangement.

In another exemplary variation of the present invention the beam selecting arrangement may be an optical fiber, an optical waveguide, a pinhole aperture, a combination of a lens with an optical fiber, waveguide or pinhole, and/or a spatial filter. The beam selecting arrangement can include a plurality of beam selecting elements, and the electromagnetic radiation which is transmitted by the plurality of beam selecting elements may be combined. The signal may be reflected multiple times from the continuously rotating optical arrangement before being received by the selecting arrangement.

According to yet another exemplary embodiment of the present invention the apparatus for filtering an electromagnetic radiation may include at least one spectral separating arrangement configured to angularly separate one or more components of the electromagnetic radiation based on a frequency of the electromagnetic radiation. Such arrangement can also include at least one angularly deflecting optical arrangement that includes a pivot point, and that is configured to receive the components of the electromagnetic radiation and selectively direct the components to a beam selecting arrangement. Further, the arrangement can include at least one optical imaging arrangement configured to receive the components of the electromagnetic radiation and generate an image of one or more dispersive elements associated with the components. The position of the pivot point of the angularly deflecting optical arrangement may be provided in proximity to a real or virtual image of at least one of the dispersive elements.

In one exemplary variant of the present invention, a deflection point of the angularly deflecting optical element may substantially overlap with a real image of at least one of the dispersive elements. At least one reflector which is configured to receive at least one signal from the at least one angularly deflecting optical arrangement may also be provided. One or more of the dispersive elements may be a diffraction grating, a prism, a grism, an acousto-optic beam deflector, a virtual phased array, and/or an arrayed waveguide grating. The angularly deflecting optical element may be a polygon mirror scanner, a galvanometer mirror scanner, or a piezo-electric mirror scanner.

According to still another exemplary embodiment of the present invention, an apparatus is provided for filtering an electromagnetic radiation. The apparatus includes at least one dispersive arrangement configured to angularly separate components of the electromagnetic radiation based on a frequency of the electromagnetic radiation, and generate frequency-separated components. The apparatus may also include at least one angularly deflecting optical element having a pivot point of an angular deflection. The pivot point can substantially overlap a location where substantially all of the frequency-separated components overlap.

In another exemplary embodiment of the present invention, at least one spectral separating arrangement can be provided that is configured to physically separate one or more components of the electromagnetic radiation based on a frequency of the electromagnetic radiation. In addition, at least one continuously rotating optical arrangement may be included which is configured to receive at least one signal that is associated with the one or more components. At least one beam selecting arrangement may also be configured to receive the signal. The emitter can be a laser gain medium, a semiconductor optical amplifier, a laser diode, a super-luminescent diode, a doped optical fiber, a doped laser crystal, a doped laser glass, and/or a laser dye.

In still another exemplary embodiment of the present invention, a source arrangement can provide an electromagnetic radiation. The source includes at least one emitter of the electromagnetic radiation, at least one spectral separating arrangement configured to angularly separate one or more components of the electromagnetic radiation based on a frequency of the electromagnetic radiation, as well as at least one angularly deflecting optical arrangement that includes a pivot point, and configured to receive the components of the electromagnetic radiation to generate at least one signal associated with the one or more components. In addition, the source arrangement can include at least one beam selecting arrangement adapted to receive the signal, and selectively generate at least one selected signal, and at least one optical imaging arrangement configured to received the selected signal, and generate an image of one or more dispersive elements associated with the one or more components. In a variation of the present invention, more than one laser gain medium providing electromagnetic radiation and at least one spectral separating arrangement configured to physically separate one or more components of the electromagnetic radiation based on a frequency of the electromagnetic radiation can be provided. In this variation, the selected components of electromagnetic radiation from each laser gain medium are synchronized, and can be used separately or combined.

In one further exemplary embodiment of the present invention, a high-speed tuning of an extended-cavity semiconductor laser may be provided. The laser resonator may include a unidirectional fiber-optic ring, a semiconductor optical amplifier as the gain medium, and a scanning filter based on a polygon scanner. Variable tuning rates of up to 1,150 nm/ms (15.7 kHz repetition frequency) can be obtained over a 70 nm wavelength span centered at 1.32 µm. Such tuning rate can be more than an order of magnitude faster than is conventionally know, and may be facilitated in part by self-frequency shifting in the semiconductor optical amplifier. The instantaneous line width of the source may be <0.1 nm for 9-mW cw output power, and a low spontaneous-emission background of 80 dB can be obtained.

Other features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 1G is a block diagram of a seventh exemplary embodiment of the optical wavelength filter according to the present invention;

DETAILED DESCRIPTION

Figure 1A:
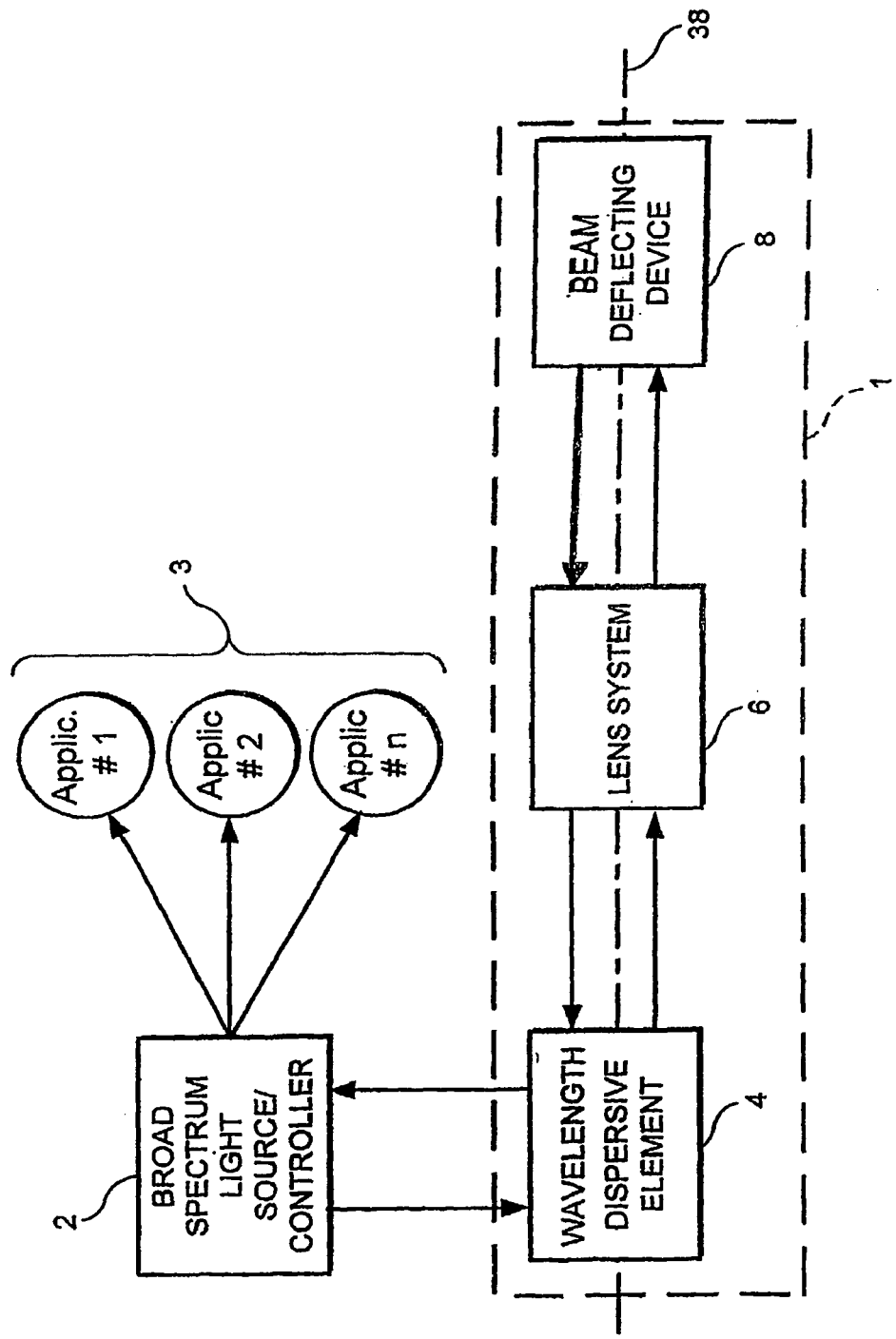
FIG. 1A is a block diagram of a first exemplary embodiment of an optical wavelength filter according to the present invention.

FIG. 1A shows a block diagram of a first exemplary embodiment of an optical wavelength filter 1 in accordance the present invention. In this first exemplary embodiment, the optical wavelength filter 1 can be used in a variety of different applications, general examples of which are described below. In this example, the filter 1 may be coupled to one or more applications 3 via a light source 2. It should be understood that in certain exemplary applications, the filter 1 can be used with or connected to an application (e.g., one or more of the applications 3) via a device other than a light source (e.g. a passive or active optical element). In the first exemplary embodiment shown in FIG. 1A, a broad spectrum light source and/or controller 2 (hereinafter referred to as "light controller"), may be coupled to a wavelength dispersing element 4. The light controller 2 can be further coupled to one or more of the applications 3 that are adapted to perform one or more tasks with or for, including but not limited to, optical imaging processes and optical imaging systems, laser machining processes and systems, photolithography and photolithographic systems, laser topography systems, telecommunications processes and systems, etc. The wavelength dispersing element 4 can be coupled to a lens system 6, which is further coupled to a beam deflection device 8.

The light controller 2 can be one or more of various systems and/or arrangements that are configured to transmit a beam of light having a broad frequency (f) spectrum. In one exemplary embodiment, the beam of light may be a collimated beam of light The beam of light can include a plurality of wavelengths λ . . . λn, within the visible light spectrum (e.g., red, blue, green). Similarly, the beam of light provided by the light controller 2 can also include a plurality of wavelengths λ . . . λn that may be defined outside of the visible spectrum (e.g., ultraviolet, near infrared or infrared). In one exemplary embodiment of the present invention, the light controller 2 can include a unidirectional light transmission ring, which shall be described in further detail below in connection with FIG. 3 which shows an exemplary embodiment of a wavelength tuning laser source. Further, in another exemplary embodiment of the present invention, the light controller 2 can include a linear resonator system, which shall be described in further detail below in connection with FIG. 6.

The wavelength dispersing element 4 of the optical wavelength filter 1 can include one or more elements that are specifically adapted to receive the beam of light from the light controller 2, and to conventionally separate the beam of light into a plurality of wavelengths of light having a number of directions. The wavelength dispersing element 4 is further operative to direct portions of light having different wavelengths in equal angular directions or displacements with respect to an optical axis 38. In one exemplary embodiment of the present invention, the wavelength dispersing element 4 can include a light dispersion element, which may include but not limited to, a reflection grating, a transmission grating, a prism, a diffraction grating, an acousto-optic diffraction cell or combinations of one or more of these elements.

The lens system 6 of the optical wavelength filter 1 can include one or more optical elements adapted to receive the separated wavelengths of light from the wavelength dispersing element. Light at each wavelength propagates along a path which is at an angle with respect to the optical axis 38. The angle is determined by the wavelength dispersing element 4. Furthermore, the lens system 6 is adapted to direct or steer and/or focus the wavelengths of light to a predetermined position located on a beam deflection device 8.

The beam deflection device 8 can be controlled to receive and selectively redirect one or more discrete wavelengths of light back along the optical axis 38 through the lens system 6 to the wavelength dispersing element 4 and back to the light controller 2. Thereafter, the light controller 2 can selectively direct the received discrete wavelengths of light to any one or more of the applications. The beam deflecting device 8 can be provided in many different ways. For example, the beam deflecting device 8 can be provided from elements including, but not limited to, a polygonal mirror, a planar mirror disposed on a rotating shaft, a mirror disposed on a galvanometer, or an acousto-optic modulator.

Figure 1B:
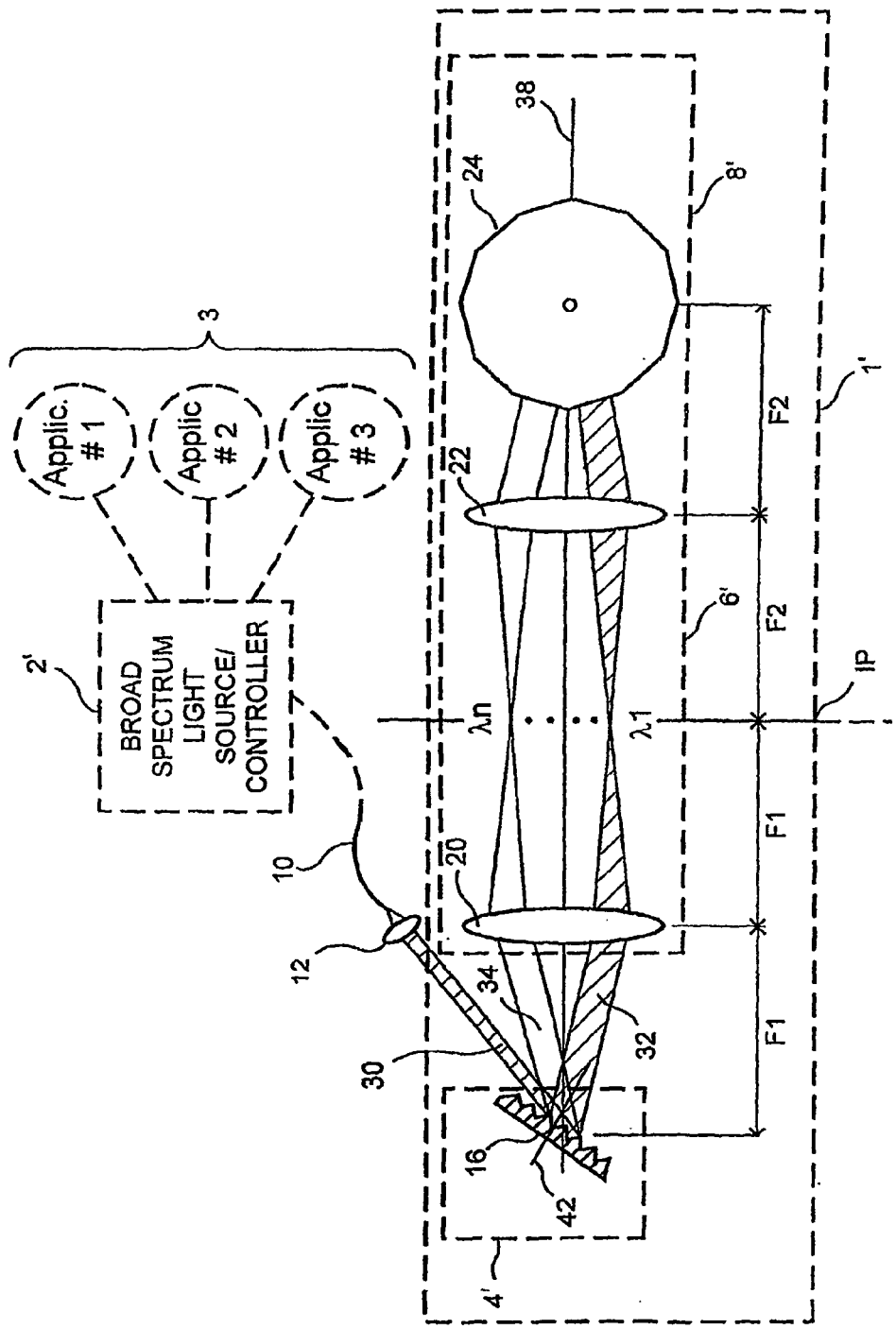
FIG. 1B is a block diagram of a second exemplary embodiment of the optical wavelength filter according to the present invention.

FIG. 1B shows a schematic diagram of a second exemplary embodiment of the optical wavelength filter 1'. The exemplary optical wavelength filter 1' can be configured as a reflection-type filter which may have substantially identical input and output ports. An input/output optical fiber 10 and a collimating lens 12 can provide an input from a light controller 2' (which may be substantially similar to the light controller 2 described above with reference to FIG. 1A) to the optical wavelength filter 1'. The optical wavelength filter 1' includes a diffraction grating 16, optical telescoping elements 6' (hereinafter referred to as "telescope 6'" and may possibly be similar to the lens system 6 of FIG. 1A), and a polygon mirror scanner 24. The telescope 6' can include two lenses, e.g., first and second lenses 20, 22 with 4-f configuration.

In the second exemplary embodiment of the optical wavelength filter 1' shown in FIG. 1B, the telescope 6' includes the first and second lenses 20, 22, which are each substantially centered along the optical axis 38. The first lens 20 may be located at a first distance from the wavelength dispensing element 4' (e.g., diffraction grating 16), which can approximately be equal to the focal length F1 of the first lens 20. The second lens 22 may be located at a second distance from the first lens 20, which can be approximately equal to the sum of the focal length F1 of the first lens 20 and the focal length F2 of the second lens 22. Using such arrangement, the first lens 20 can receive one or more collimated discrete wavelengths of light from the wavelength dispersing element 4', and can effectively perform a Fourier Transform on each one of the collimated one or more discrete wavelengths of light to provide one or more approximately equal converging beams that are projected onto an image plane IP.

The image plane IP is preferably located between the first lens 20 and the second lens 22 and at a predetermined distance from the first lens 20. According to one exemplary variation of the present invention, such predetermined distance may be defined by the focal length F1 of the first lens 20. After such one or more converging beams are propagated through the image plane IP, these one or more converging beams form equal or corresponding one or more diverging beams that are received by the second lens 22. The second lens 22 is adapted to receive the diverging beams and provide approximately an equal number of collimated beams having predetermined angular displacements with respect to the optical axis 38. Thus, the second lens 22 can direct or steer the collimated beams to predefined portions of the beam deflection device 8'.

The telescope 6' according to the second exemplary embodiment of the present invention is operative to provide one or more features as described above, as well as to convert a diverging angular dispersion from the grating into converging angular dispersion after the second lens 22. Such result may be advantageous for a proper operation of the filter. In addition, the telescope 6' may provide adjustable parameters which control the tuning range and linewidth and reduce the beam size at the polygon mirror to avoid beam clipping. As is illustrated in the exemplary embodiment of FIG. 1B, a beam deflection device 6' (e.g., which may include a polygon mirror or arrangement 24) is adapted to preferably reflect back only the spectral component within a narrow passband as a function of the angle of the front mirror facet of the polygon arrangement 24 with respect to the optic axis 38. The reflected narrow band light is diffracted and received by the optical fiber 10. The orientation of the incident beam 30 with respect to the optic axis and a rotation direction 40 of the polygon arrangement 24 can be used to determine the direction of wavelength tuning, e.g., a wavelength up (positive) scan or a wavelength down (negative) scan. The exemplary arrangement shown in FIG. 1B can generate a positive wavelength sweep. It should be understood that although the polygon arrangement 24 is shown in FIG. 1B as having twelve facets, polygon arrangements which have fewer than twelve facets or greater than twelve facets can also be used. While generally not considering practical mechanical limits, based upon conventional manufacturing techniques, a particular number of facets of the polygon arrangement 24 to use in any application may depend on a desired scanning rate and a scanning range for a particular application.

Furthermore, the size of the polygon arrangement 24 may be selected based on preferences of a particular application, and preferably taking into account certain factors including, but not limited to, manufacturability and weight of the polygon arrangement 24. It should also be understood that lenses 20, 22 that have different focal lengths may be provided. For example, the lenses 20, 22 should be selected to provide a focal point at approximately the center point 24a of the polygon arrangement 24.

In one exemplary embodiment, a Gaussian beam 30 can be utilized with a broad optical spectrum incident to the grating from the fiber collimator 12. The well-known grating equation is expressed as $\lambda = p \cdot (\sin \alpha + \sin \beta)$ where $\lambda$ is the optical wavelength, p is the grating pitch, and $\alpha$ and $\beta$ are the incident and diffracted angles of the beam with respect to the normal axis 42 of the grating, respectively. The center wavelength of tuning range of the filter may be defined by $\lambda_0 = p \cdot (\sin \alpha + \sin \beta_0)$ where $\beta_0$ is the angle between the optic axis 38 of the telescope and the grating normal axis. FWHM bandwidth of the filter is defined by $(\delta\lambda)_{FWHM}/\lambda_0 = A \cdot (p/m) \cos \alpha /W$, where $A = \sqrt{4\ln 2}/\pi$ for double pass, m is the diffraction order, and W is $1/e^2$-width of the Gaussian beam at the fiber collimator.

Tuning range of the filter may be limited by the finite numerical aperture of the first lens 20. The acceptance angle of the first lens 20 without beam clipping may be defined by $\Delta\beta = (D_1 - W \cos \beta_0/\cos \alpha)/F_1$, where $D_1$ and $F_1$ are the diameter and focal length of the first lens 20. Such formulation relates to the filter tuning range via $\Delta\lambda = p \cos \beta_0 \cdot \Delta\beta$. One of exemplary design parameters of the filter, originated from the multiple facet nature of the polygon mirror, is the free spectral range, which is described in the following. A spectral component after propagating through the first lens 20 and the second lens 22 may have a beam propagation axis at an angle $\beta'$ with respect to the optic axis 38, e.g., $\beta' = -(\beta - \beta_0) \cdot (F_1/F_2)$, where $F_1$ and $F_2$ are the focal lengths of the first lens 20 and the second lens 22, respectively. The polygon arrangement 24 may have a facet-to-facet polar angle given by $\theta = 2\pi/N \approx L/R$, where L is the facet width, R is the radius of the polygon and N is the number of facets. If the range of $\beta'$ of incident spectrum is greater than the facet angle, i.e. $\Delta\beta' = \Delta\beta \cdot (F_1/F_2) > \theta$, the polygon arrangement 24 can retro-reflect more than one spectral component at a given time. The spacing of the multiple spectral components simultaneously reflected, or the free spectral range, can be defined as $(\Delta\lambda)_{FSR} = p \cos \beta_0 (F_1/F_2) \cdot \theta$. In an exemplary intra-cavity scanning filter application, the free spectral range of the filter should exceed the spectral range of the gain medium in order to avoid multiple frequency bands (in the case of an inhomogeneously broadened gain medium) or limited tuning range (in the case of a homogeneously broadened gain medium).

The duty cycle of laser tuning by the filter can be, for example, 100% with no excess loss caused by beam clipping if two preferable conditions are met as follows:

$$W < \frac{\cos\alpha F_1}{\cos\beta F_2} L \text{ and } W < \frac{\cos\alpha}{\cos\beta_0}(F_2 - S) \cdot \theta \quad (1)$$

The first equation may be derived from a condition that the beam width after the second lens 22 should be smaller than the facet width. The second equation can be derived from that the two beams at the lowest 32 and highest wavelengths 34 of the tuning range, respectively, which should not overlap each other at the polygon arrangement 24. S in equation (1) denotes the distance between the second lens 22 and the front mirror of the polygon arrangement 24.

It is possible to select the optical components with the following parameters: W=2.4 mm, p=1/1200 mm, $\alpha$=1.2 rad, $\beta_0$=0.71 rad, m=1, $D_1$=$D_2$=25 mm, $F_1$=100 mm, $F_2$=45 mm, N=24, R=25 mm, L=6.54, S=5 mm, $\theta$=0.26 rad, $\lambda_0$=1320 nm. From the parameters, the theoretical FWHM bandwidth, tuning range and free spectral range of the filter could be calculated: $(\delta\lambda)_{FWHM}$=0.09 nm, $\Delta\lambda$=126 nm and $(\Delta\lambda)_{FSR}$=74 nm. Both conditions in equation (1) may be satisfied with particular margins.

Figure 1C:
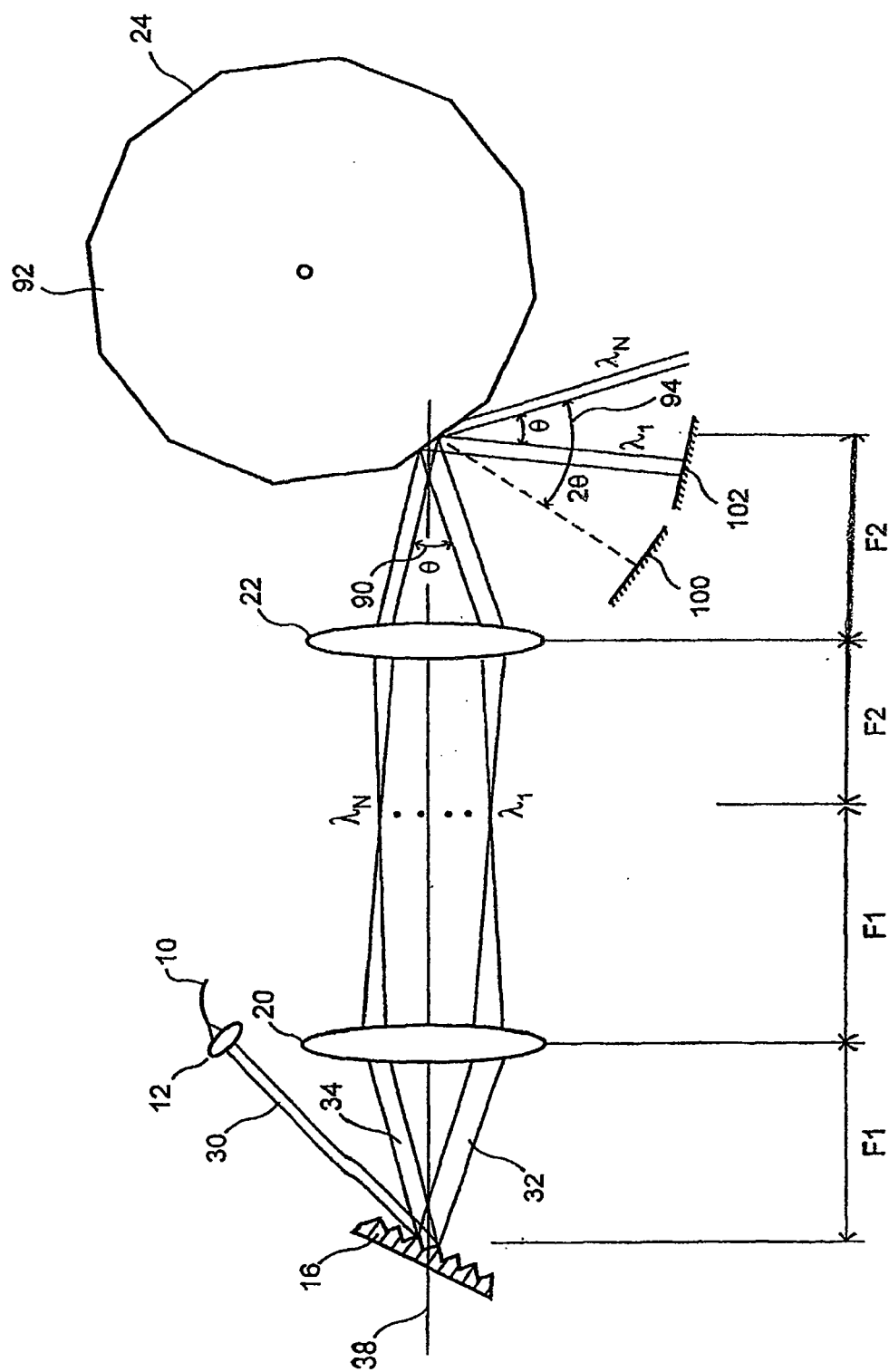
FIG. 1C is a block diagram of a third exemplary embodiment of the optical wavelength filter according to the present invention.

FIG. 1C shows a diagram of a third exemplary embodiment of the wavelength tunable filter arrangement for doubling the tuning speed with the same polygon rotation speed according to the present invention. In this exemplary embodiment, the mirror surface of the polygon arrangement 24 is placed substantially a distance F2 from lens 22, and the beam of light is reflected with a non-zero angle (rather than directly being reflected back to the telescope from the polygon arrangement's 24 mirror facet). The sweep angle of the reflected light from the polygon arrangement 24 is double the polygon arrangement's 24 rotation angle. When the incident angle difference 90 between $\lambda_1$ and $\lambda_N$ with respect to the polygon arrangement 24 is approximately the same as the facet-to-facet angle 92 of the polygon, e.g., angle $\theta$, the sweep angle 94 of the reflected light is $2\theta$ for a rotation of the angle $\theta$ of the polygon arrangement 24. By placing two reflectors 100, 102, which preferably direct the reflected beam of light from the polygon arrangement 24 back to the polygon arrangement 24, and to the telescope (e.g., similar to the telescope 6' of FIG. 1B), with the angle θ between each other, twice wavelength scans from $\lambda_1$ to $\lambda_N$ are achieved for the polygon rotation of the one facet-to-facet angle θ.

Figure 1D:
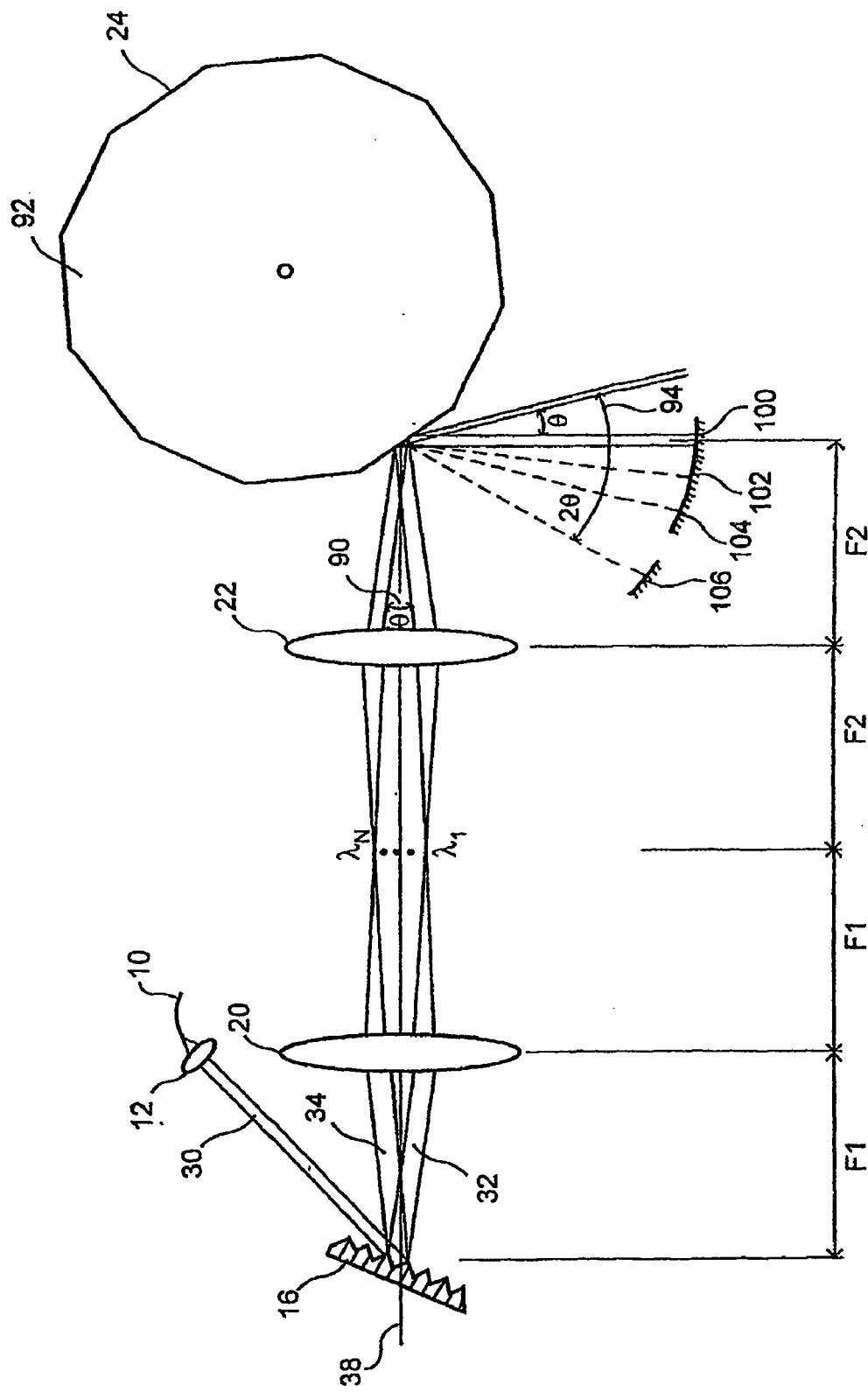
FIG. 1D is a block diagram of a fourth exemplary embodiment of the optical wavelength filter according to the present invention.

In FIG. 1D which shows a fourth exemplary embodiment of the present invention, the incident angle 90 difference between $\lambda_1$ and $\lambda_N$ to the polygon arrangement 24 is smaller than polygon facet-to facet angle 92, e.g., φ (=θ/K, where K>1). This can be achieved by reducing the grating pitch and increasing the F2/F1 ratio. In this exemplary embodiment, the filter tuning speed may be increased by factor of 2K without increasing either the rotation speed of the polygon arrangement 24 or the number of facets of the polygon arrangement 24.

Figure 1E:
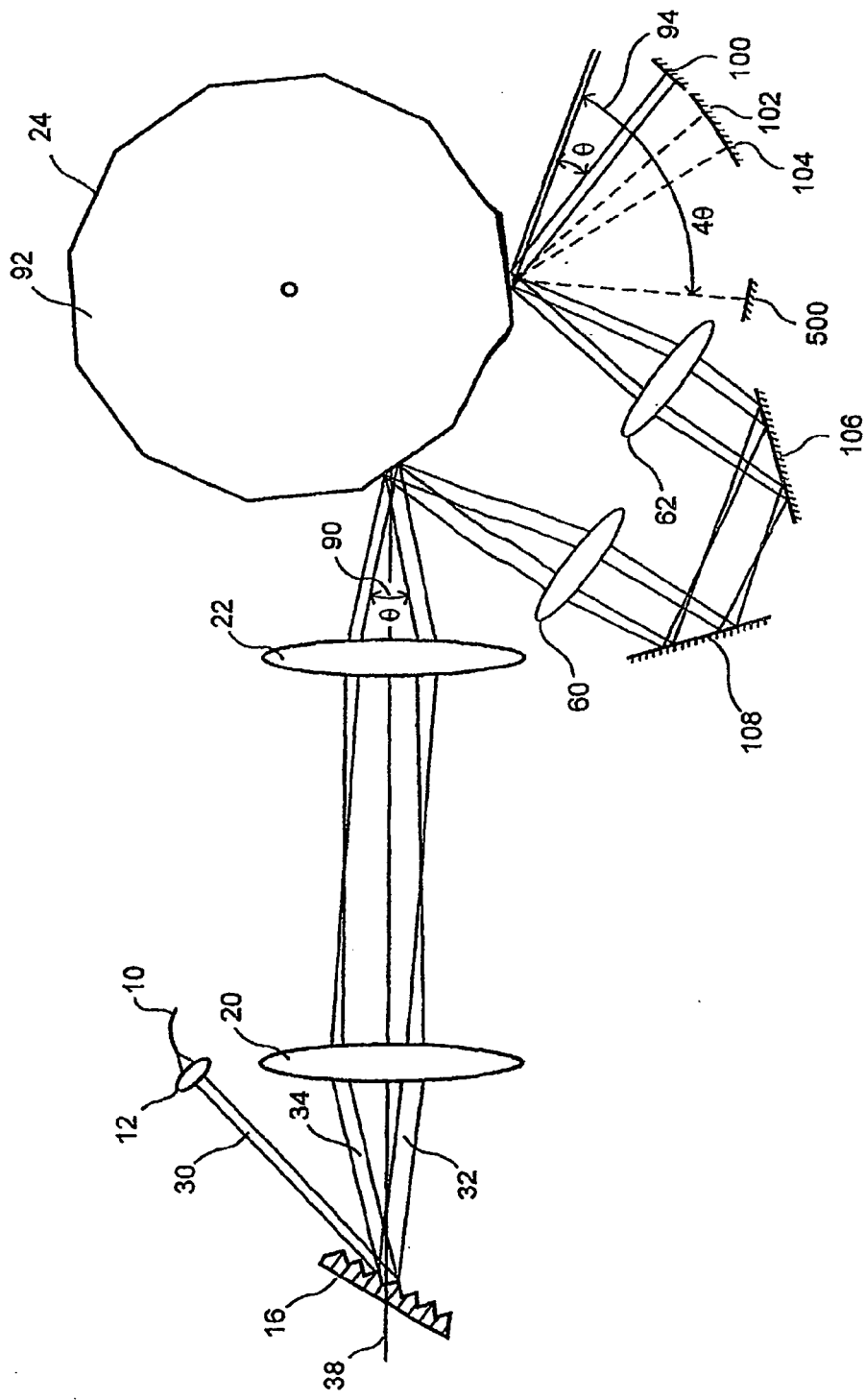
FIG. 1E is a block diagram of a fifth exemplary embodiment of the optical wavelength filter according to the present invention.

The filter tuning speed can be further increased by having the beam of light reflected multiple times by the polygon arrangement 24. A fifth exemplary embodiment of the present invention, depicted in FIG. 1E, is an arrangement for increasing the tuning speed by factor of 4K, where K is the ratio of angle 92 to angle 90 (K=θ/φ). The beam of light is reflected twice (e.g., four times round trip) by the polygon arrangement 24, so that the sweep angle 94 of the reflected light becomes angle 4θ, and the tuning speed becomes 4K times faster. Such reflection can also be assisted with the reflection of surfaces 100, 102, 104, 106 and 108. This exemplary embodiment of the filter arrangement can be used to broaden the free spectral range ("FSR") of the filter. For example, if one of the final reflectors 102 in the embodiment shown in FIG. 1E is removed, the FSR of the filter may become twice broader. It is likely that there is no tuning speed enhancement in such case. Similarly, it is possible to retain only one final reflector 100 in FIG. 1E. The FSR in this embodiment can become four times broader.

Figure 1F:
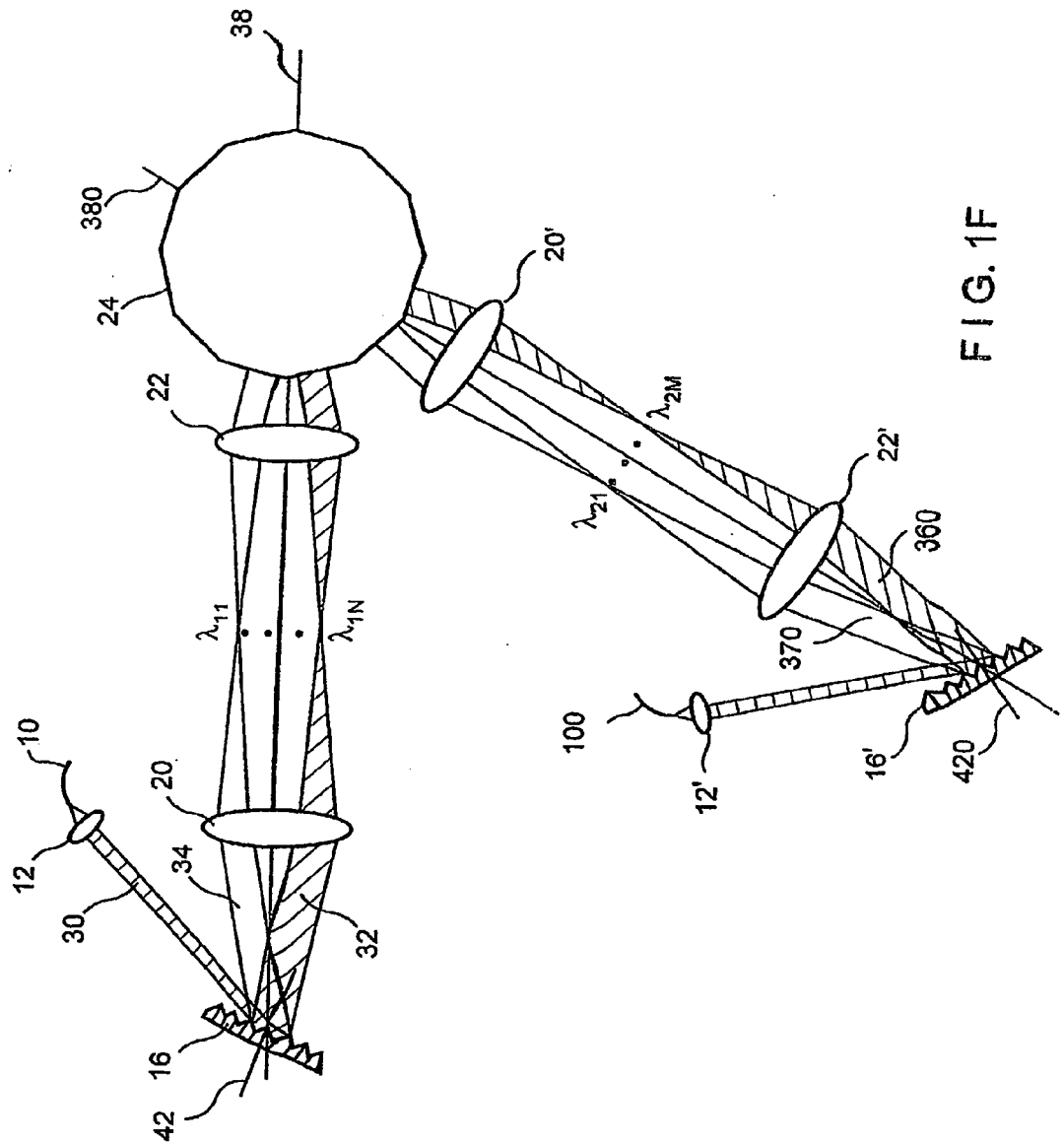
FIG. 1F is a block diagram of a sixth exemplary embodiment of the optical wavelength filter according to the present invention.

FIG. 1F shows a sixth exemplary embodiment of the present invention which provides a polygon tuning filter accommodating two light inputs and outputs. For example, in order to support two or more inputs and outputs of this filter, two or more sets of optical arrangements, each respective set including an input/output fiber 10, 10', a collimating lens 12, 12', a diffraction grating 16, 16', and a telescope, may share the same polygon arrangement 24. Because the scanning mirror of the polygon arrangement 24 is structurally isotropic about the rotation axis, certain optical arrangements that can deliver the beams of light to the polygon arrangement 24 can be accommodated from any directions. Since both sets of optical arrangement in the embodiment of FIG. 1F utilize the same polygon scanner, their respective scanning optical transmission spectra are synchronized. It should be understood that the exemplary embodiment of FIG. 1F can be extended to include multiple (greater than 2) optical arrangements each having its own input and output optical channel.

One exemplary application of the above-described polygon tuning filter according to the sixth embodiment of the present invention may be a wide band wavelength scanning light source. In FIG. 1G which shows a seventh exemplary embodiment of the present invention, a first broadband light source 60 provides a light signal which may have a wavelength $\lambda_1$ to $\lambda_i$, and a second broadband light source 600 provides another light signal having a wavelength $\lambda_{i-j}$ to $\lambda_N$. When the two optical arrangements supporting the wavelengths $\lambda_1$ to $\lambda_i$ and the wavelengths $\lambda_{i-j}$ to $\lambda_N$, respectively, are synchronized to output approximately the same wavelength at the same instance, such exemplary arrangement may become a wide band wavelength scanning light source with linear scan rate from $\lambda_1$ to $\lambda_N$. Since the FSR of the polygon scanning filter can be adjusted to be 200 nm or wider without any optical performance degradation, two or more broadband light sources with different center wavelengths can be combined with this filter to provide linear scanning light source over 200 nm tuning bandwidth. It should be understood that the embodiment of FIG. 1G can be extended to include multiple (e.g., greater than 2) optical arrangements and multiple (e.g., greater than 2) broadband light sources.

The exemplary embodiment illustrated in FIG. 1G can also be configured so that the wavelength tuning bands of each optical arrangement and broadband light source are discontinuous. In such a configuration, the tuning bands can be swept in a continuous or discontinuous sequential manner or be swept simultaneously.

Figure 2:
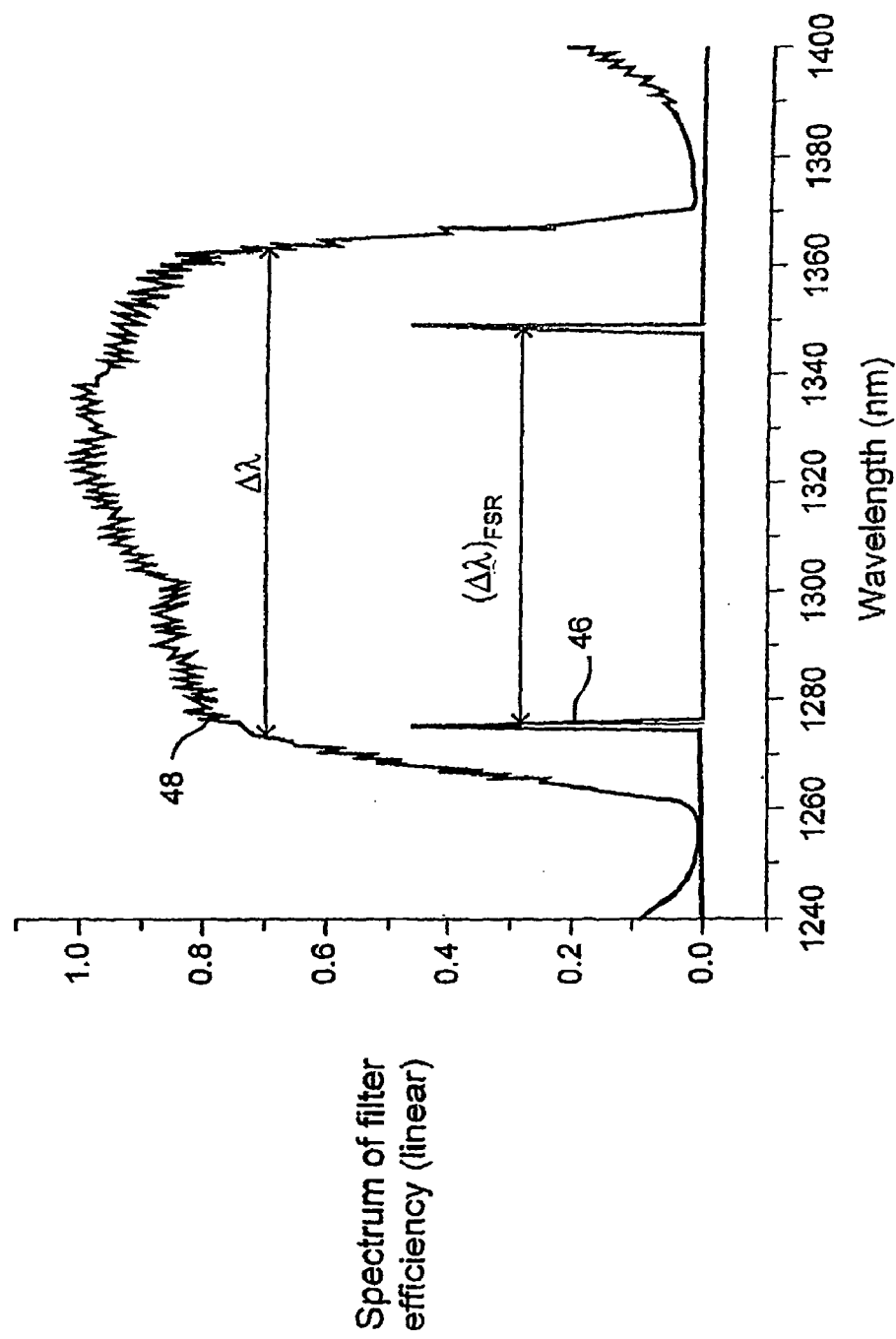
FIG. 2 is a graph of exemplary characteristics of the optical wavelength filter according to the present invention.

FIG. 2 shows an exemplary graph of measured characteristics of the filter according to an exemplary embodiment of the present invention. The normalized reflection spectrum of the filter, e.g., a curve 48, may be measured by using broadband amplifier spontaneous emission light from a semiconductor optical amplifier (SOA) and an optical spectrum analyzer. The optical spectrum analyzer can obtain or record a normalized throughput (reflected) spectrum in peak-hold mode while the polygon arrangement 24 spins at its maximum speed of 15.7 kHz. The measured tuning range may be 90 nm which is substantially smaller than the theoretical value of 126 nm. It is possible to have a discrepancy which may be due to an aberration of the telescope 6', primarily field curvature, associated with relatively large angular divergence of the beam from the grating. Such aberration can be corrected using optimized lens designs well known in the art. A curve 46 shown in FIG. 2 illustrates the throughput spectrum when the polygon arrangement is static at a particular position. The observed free spectral range is 73.5 nm, in agreement with a theoretical calculation. The FWHM bandwidth of curve 46 was measured to be 0.12 nm. The discrepancy between the measured FWHM and the theoretical limit of 0.09 nm is reasonable considering the aberration and imperfection of the optical elements.

Figure 3:
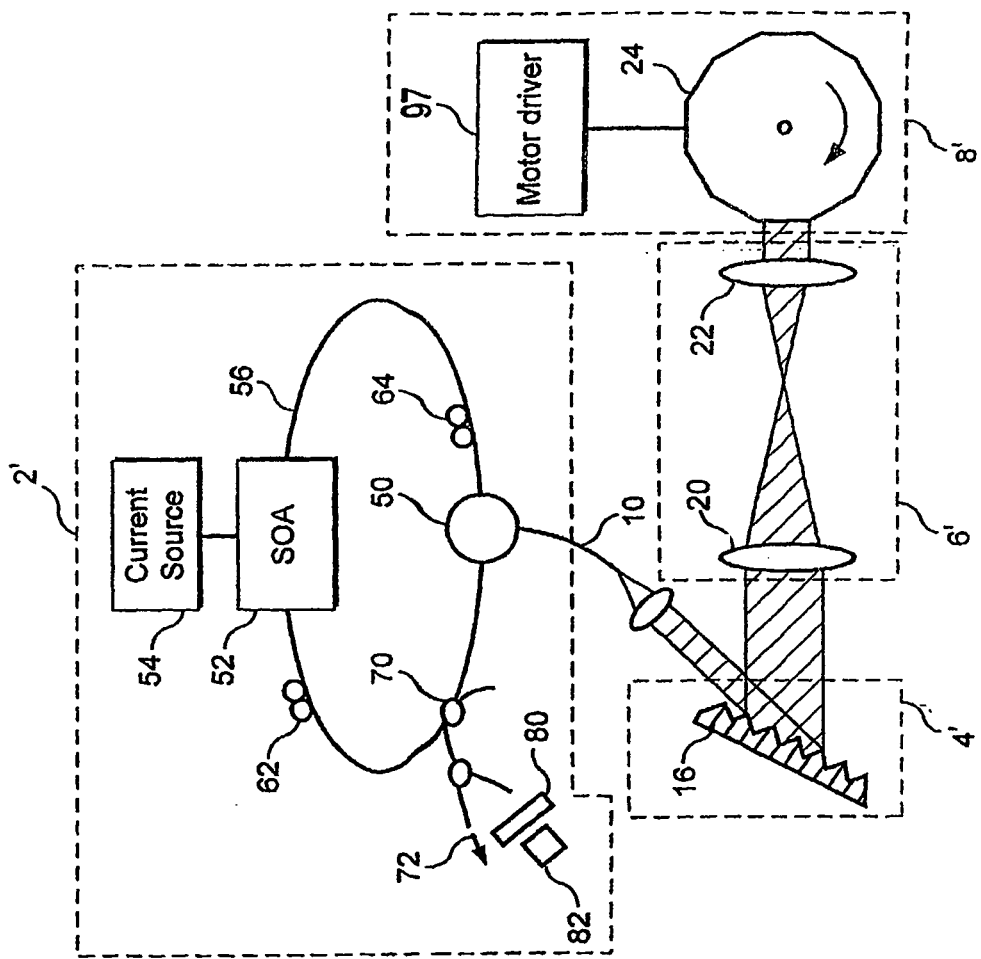
FIG. 3 is an exemplary embodiment of the wavelength tuning laser source according to the present invention.

FIG. 3 shows an exemplary embodiment of the wavelength tuning laser source according to the present invention. For example, the polygon-based filter can be incorporated into an extended-cavity semiconductor laser via a Faraday circulator 50. Intra-cavity elements may be connected by single-mode optical fibers 10. The gain medium may be a semiconductor optical amplifier 52 (e.g., SOA, Philips, CQF 882/e). Laser output 72 may be obtained via the 90% port of a fiber-optic fused coupler 70. Two polarization controllers 64, 62 can be used to align the polarization states of the intra-cavity light to the axes of maximum efficiency of the grating 16, and of the maximum gain of the SOA 50. A current source 54 may provide an injection current to the SOA 50. The polygon arrangement 24 may be driven and controlled by a motor driver 97. To generate a sync signal useful for potential applications, approximately 5% of the laser output may be directed to a photodetector 82 through a variable wavelength filter 80 with bandwidth of 0.12 nm. In this exemplary implementation, the center wavelength of the filter was fixed at 1290 nm. The detector signal can generate short pulses when the output wavelength of the laser is swept through the narrow passband of the fixed-wavelength filter. The timing of the sync pulse may be controlled by changing the center wavelength of the filter.

Figure 4A:
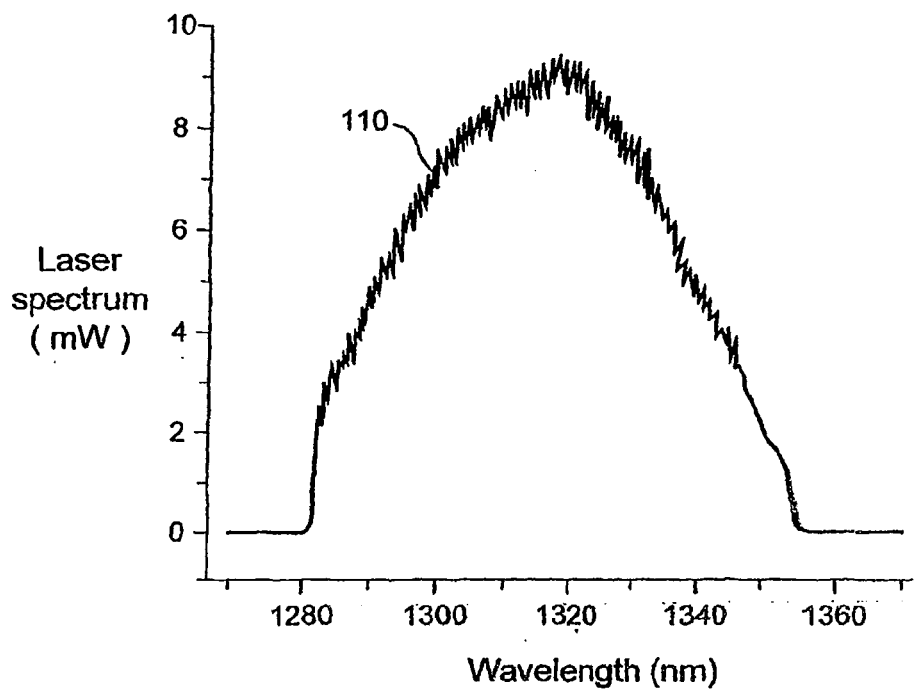
FIG. 4A is a graph of exemplary first output characteristics (laser spectrum vs. wavelength) of the laser source according to the present invention.
Figure 4B:
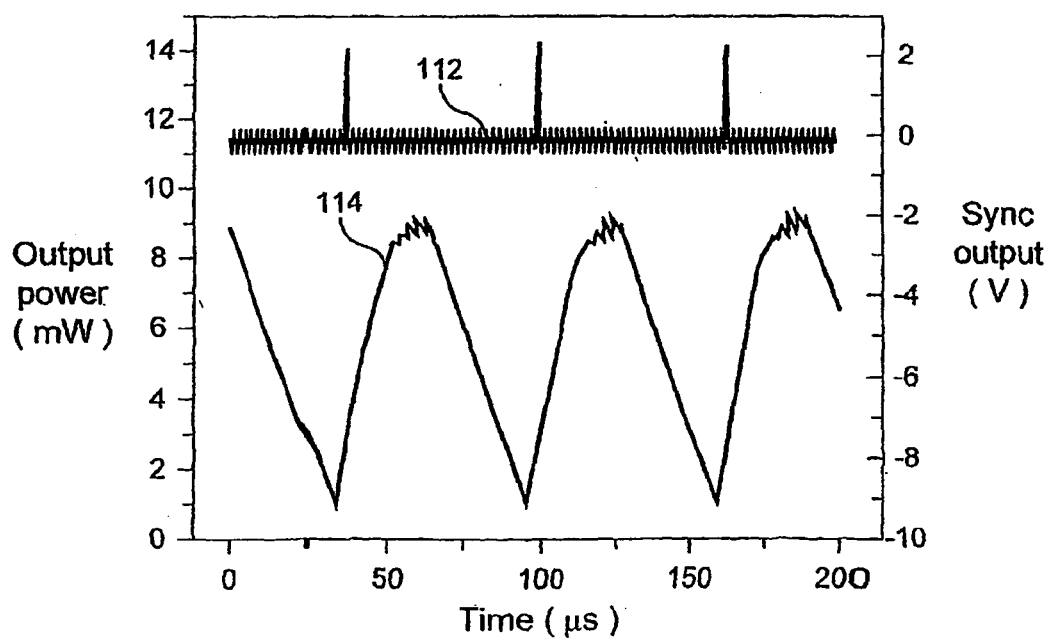
FIG. 4B is a graph of exemplary second output characteristics (output power vs. time) of the laser source according to the present invention.

FIG. 4A shows a graph of exemplary first output characteristics (laser spectrum vs. wavelength) of the laser source according to the present invention, and FIG. 4B is a graph of exemplary second output characteristics (output power vs. time) of the laser source according to the present invention. Turning to FIG. 4A, curve 110 represents the output spectrum of the laser measured by the optical spectrum analyzer in peak-hold mode, e.g., when the polygon arrangement spins at 15.7 kHz. The edge-to-edge sweep range was observed to be from 1282 nm to 1355 nm, equal to the free-spectral range of the filter. The Gaussian-like profile of the measured spectrum, rather than a square profile, can be mainly due to the polarization-dependent cavity loss caused by polarization sensitivity of the filter and the birefringence in the cavity. It may be preferable to adjust the polarization controllers to obtain the maximum sweep range and output power. In FIG. 4B, curve 114 is the output of the exemplary laser in the time domain. The upper trace 112 is the sync signal which may be obtained through the fixed-wavelength filter. The amplitude of power variation from facet to facet was less than 3.5%. The peak and average output power was 9 mW and 6 mW, respectively. The y-axis scale of the curve 110 of FIG. 4A can be calibrated from the time-domain measurement, because the optical spectrum analyzer records a time-averaged spectrum due to the laser tuning speed being much faster than the sweep speed of the spectrum analyzer.

Figure 5:
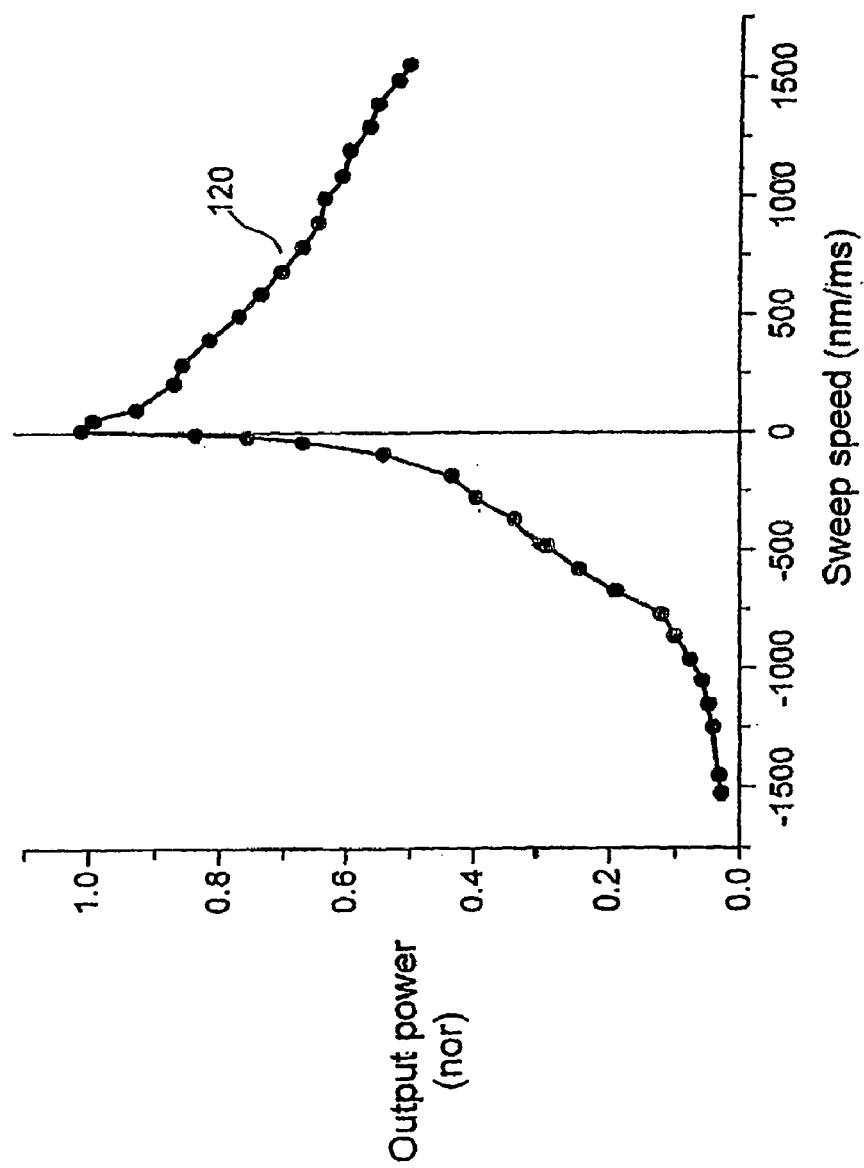
FIG. 5 is a graph of exemplary output power provided as a function of sweep speed according to the present invention.

A frequency downshift in the optical spectrum of the intra-cavity laser light may arise as the light passes through the SOA gain medium, as a result of an intraband four-wave mixing phenomenon. In the presence of the frequency downshift, greater output power can be generated by operating the wavelength scanning filter in the positive wavelength sweep direction. FIG. 5 shows an exemplary illustration of a normalized peak power of the laser output measured as a function of the tuning speed. The negative tuning speed can be obtained by flipping the position of the collimator and the orientation of the grating with respect to the optic axis 38 of the exemplary embodiment of the arrangement according to the present invention. It is preferable to make the physical parameters of the filter identical in both tuning directions. The result shows that the combined action of self-frequency shift and positive tuning allows higher output to be obtained and enables the laser to be operated at higher tuning speed as is demonstrated in the curve 120. Therefore, the positive wavelength scan may be the preferable operation. The output power can be decreased with an increasing tuning speed. A short cavity length may be desired to reduce the sensitivity of the output power to the tuning speed. In such case, a free-space laser cavity may be preferred.

Figure 6:
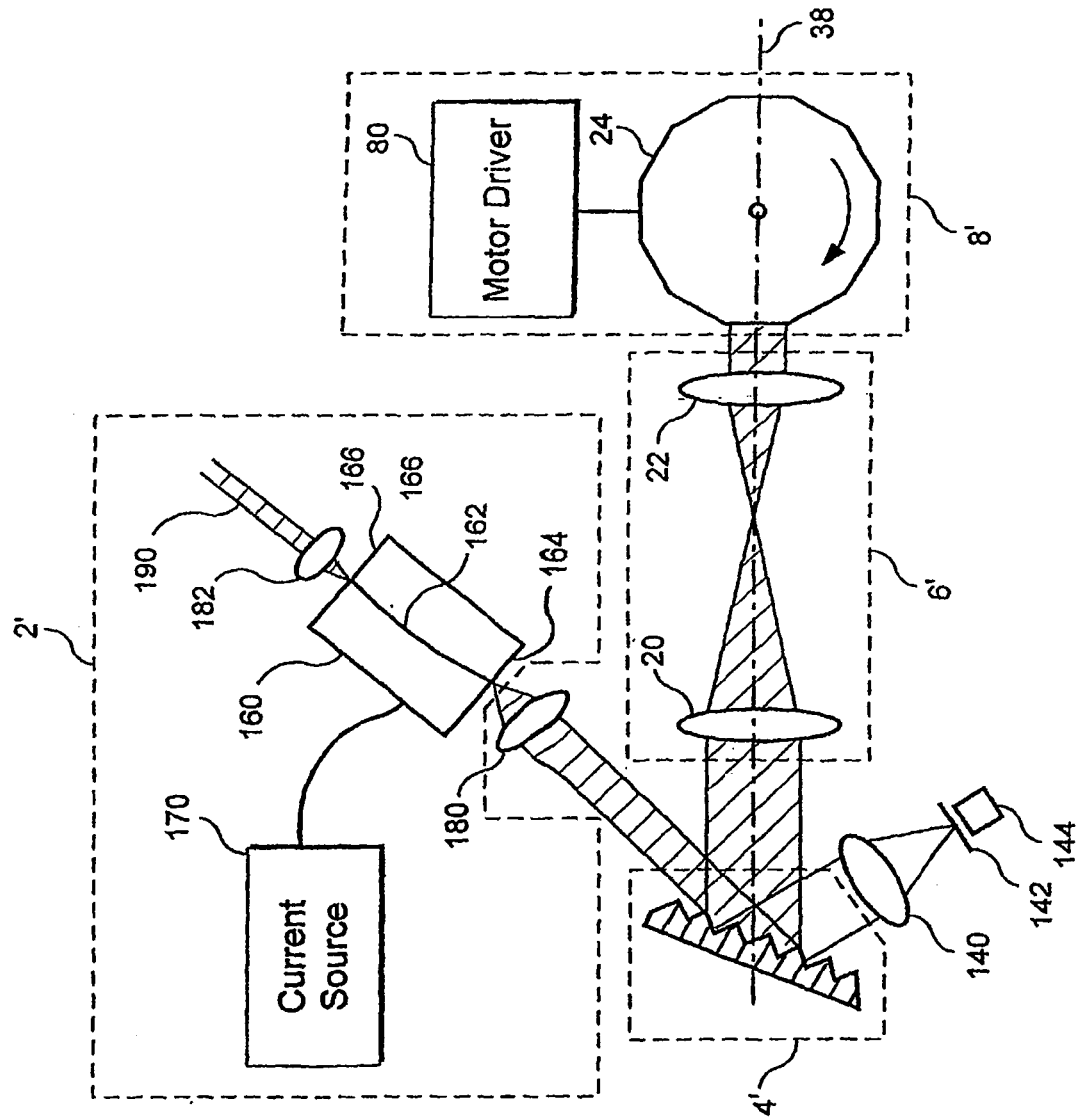
FIG. 6 is an exemplary embodiment of a free-space extended-cavity semiconductor tunable laser arrangement according to the present invention.

An exemplary embodiment of a free-space extended-cavity semiconductor tunable laser arrangement according to the present invention is depicted in FIG. 6. A semiconductor waveguide 162 made on a substrate chip 160 can be coupled to the polygon scanning filter via a collimating lens 180. The front facet 164 thereof may be anti-reflection coated, and the output facet 166 may be cleaved or preferably coated with dielectrics to have an optimal reflectivity. The laser output 190 may be obtained through the output coupling lens 182. The sync output may be taken by using a lens 140, a pinhole 142, and a photodetector 144 positioned on the 0-th order diffraction path for the light which is on retro-reflection from the polygon scanner 24. The photodetector 144 can generate a short pulse when the focus of the optical beam of a particular wavelength sweeps through the pinhole 142. Other types of gain medium include but are not limited to rare-earth-ion doped fiber, Ti:Al$_2$O$_3$, and Cr$^{3+}$:forsterite. The first and second lenses 20, 22 can be preferably achromats with low aberration particularly in field curvature and coma. The collimating lenses 180, 182 are preferably aspheric lenses.

Figure 7:
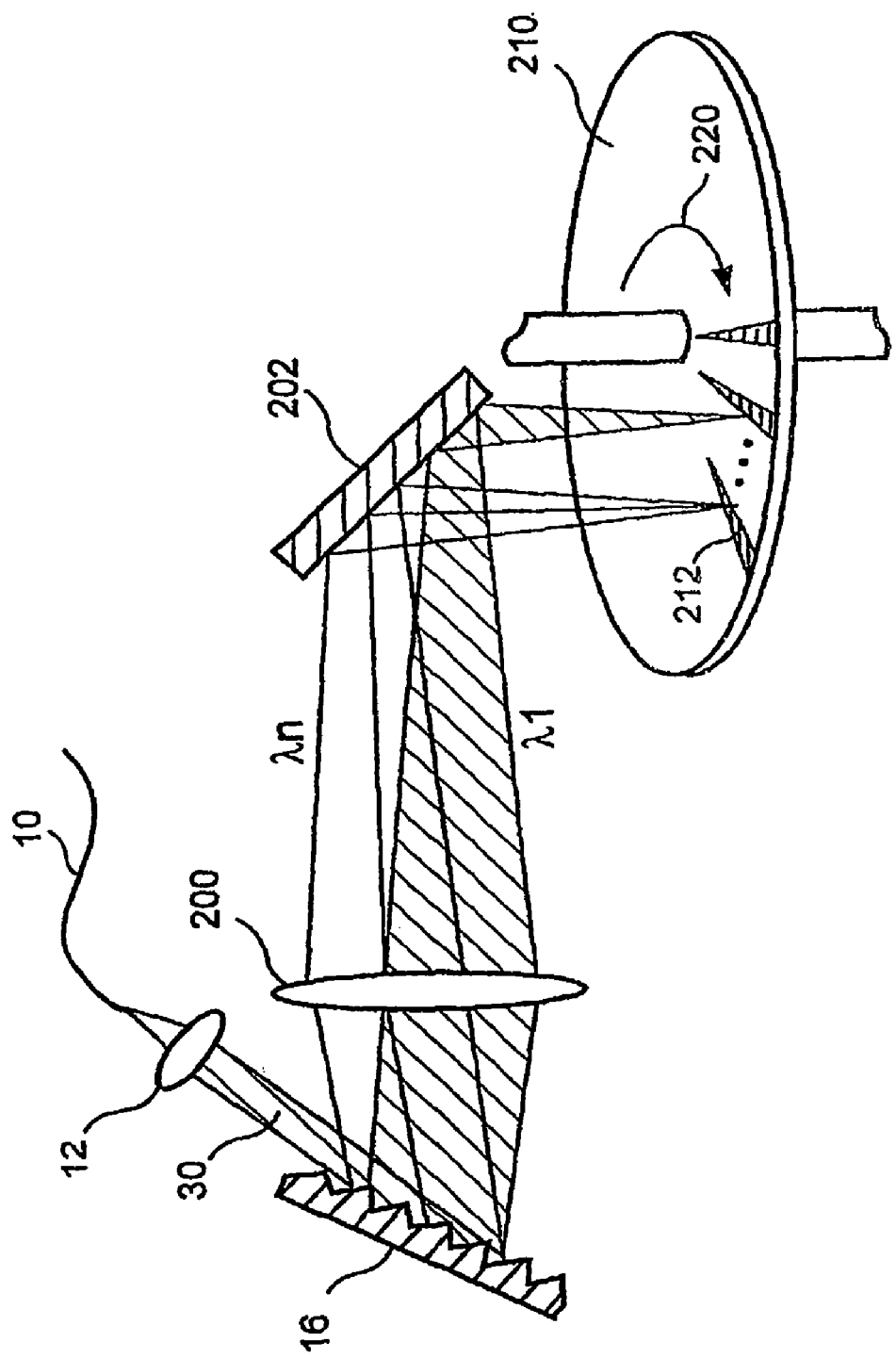
FIG. 7 is an illustration of a seventh exemplary embodiment of the optical wavelength filter according to the present invention.

FIG. 7 shows another exemplary embodiment of the wavelength tunable filter which includes an input collimating lens 12, diffraction grating 16, focusing lens 200, and a spinning disk 210, as shown in FIG. 7. The diffraction grating 16 preferably has a concave curvature that has a focal length and may thus eliminate the need for the use of the focusing lens 200. The diffraction grating may be replaced by other angular dispersive elements such as a prism. Preferably more than one reflector 212 can be deposited on the surface of the spinning disk 210. Preferably, the reflectors 212 may include multiple narrow stripes periodically and radially patterned. The material for the reflectors is preferably gold. The disk 210 can be made of a lightweight plastic or silicon substrate. Instead of the reflectors deposited on the top surface of the disk, the disk can have a series of through holes followed by a single reflector attached to the back surface of the disk or supported independently from the disk. Incident from the optical fiber 10, the optical beams of different wavelengths are illuminated on the surface of the disk into a line after being diffracted by the grating 16 and focused by the lens 200. The beam that hits the reflectors of the spinning disk may be retro-reflected and received by the optical fiber 10. For example, a mirror 202 may be used to facilitate the access of the beam onto the disk.

The distance from the lens 200 to the reflectors of the disk 210 may be approximately equal to the focal length, F, of the lens 200. The tuning range of the filter may be given by $\Delta\lambda=p \cos \beta_0 (D/F)$, where D denotes the distance between the stripes. The width of the strip, w, can preferably be substantially equal to the beam spot size, $w_s$, at the surface of the disk:

$$w_s = W \frac{\cos\beta_0}{\cos\alpha} \cdot \frac{F/z}{\sqrt{1+f/z^2}},$$

where $z=\pi w_s^2/\lambda$. Such formulation may lead to a FWHM filter bandwidth given by $(\delta\lambda)_{FWHM}/\lambda_0 = A \cdot (p/m) \cos \alpha/W$ where $A=\sqrt{4\ln2}/\pi$. For $w>w_s$, the filter bandwidth may become greater, and for $w<w_s$, the efficiency (reflectivity) of the filter can be decreased by beam clipping. The orientation of the incident beam 30 with respect to the optic axis of the lens 200 and the spinning direction 220 may determine the sense of wavelength tuning. The positive wavelength scan may be preferable, which is the case of the exemplary embodiment shown in FIG. 7.

Figure 8:
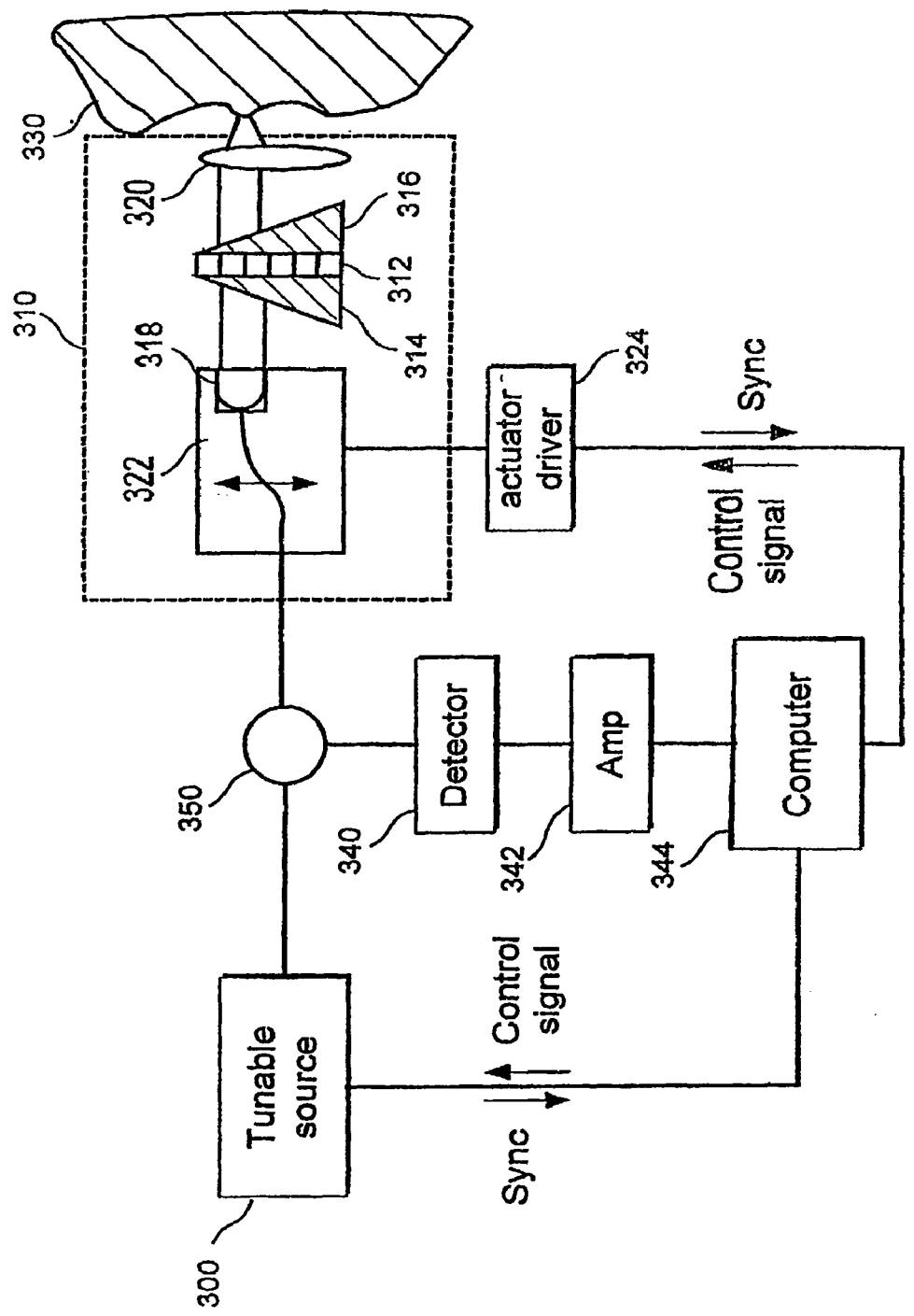
FIG. 8 is a schematic diagram of an exemplary embodiment of a spectrally-encoded confocal microscope that utilizes the tunable laser source according to the present invention.

Two exemplary applications of the exemplary embodiments of the present invention are described as follows. FIG. 8 shows a block diagram of an exemplary embodiment of the spectrally encoded confocal microscope ("SECM") that uses the aforementioned tunable laser source 300. The basic principle of SECM has been described in detail in U.S. Pat. No. 6,341,036, the disclosure of which is incorporated herein by reference in its entirety. An exemplary probe 310 includes a transmission grating 312 provided between two silicon prisms 314, 316, a collimator 318, and a microscope objective lens 320. The probe is equipped with a micro actuator 322 to scan the beam onto a different location of the sample 330. The actuator 322 may be driven by an actuator driver 324 at substantially slower speed than the tuning speed of the laser source. The probe motion is preferably rotary or translational and is synchronized to the sync output of the laser source. In one example, the wavelength sweep frequency may be 15.7 kHz, and the probe scan frequency can be 30 Hz, which allows 30 frames of image to be obtained in 1 second. The objective lens 320 has a nigh numerical aperture to provide a transverse resolution of an order of micrometers and a confocal parameter of a few micrometers. The focus of the optical beam may be continuously scanned in time over the sample 330 by the swept output wavelength of the optical source and the scanning motion of the probe. The optical power returned from the sample is proportional to the reflectivity of the sample within a small section where the beam was focused down to a narrow waist at a given time. Two dimensional en-face image of the sample is constructed by a signal processor 344. The detector 340 is preferably an avalanche photodiode ("APD") followed by a transimpedance amplifier 342. The reflected power may be received through a Faraday circulator 350 or a fiber-optic coupler.

Figure 9:
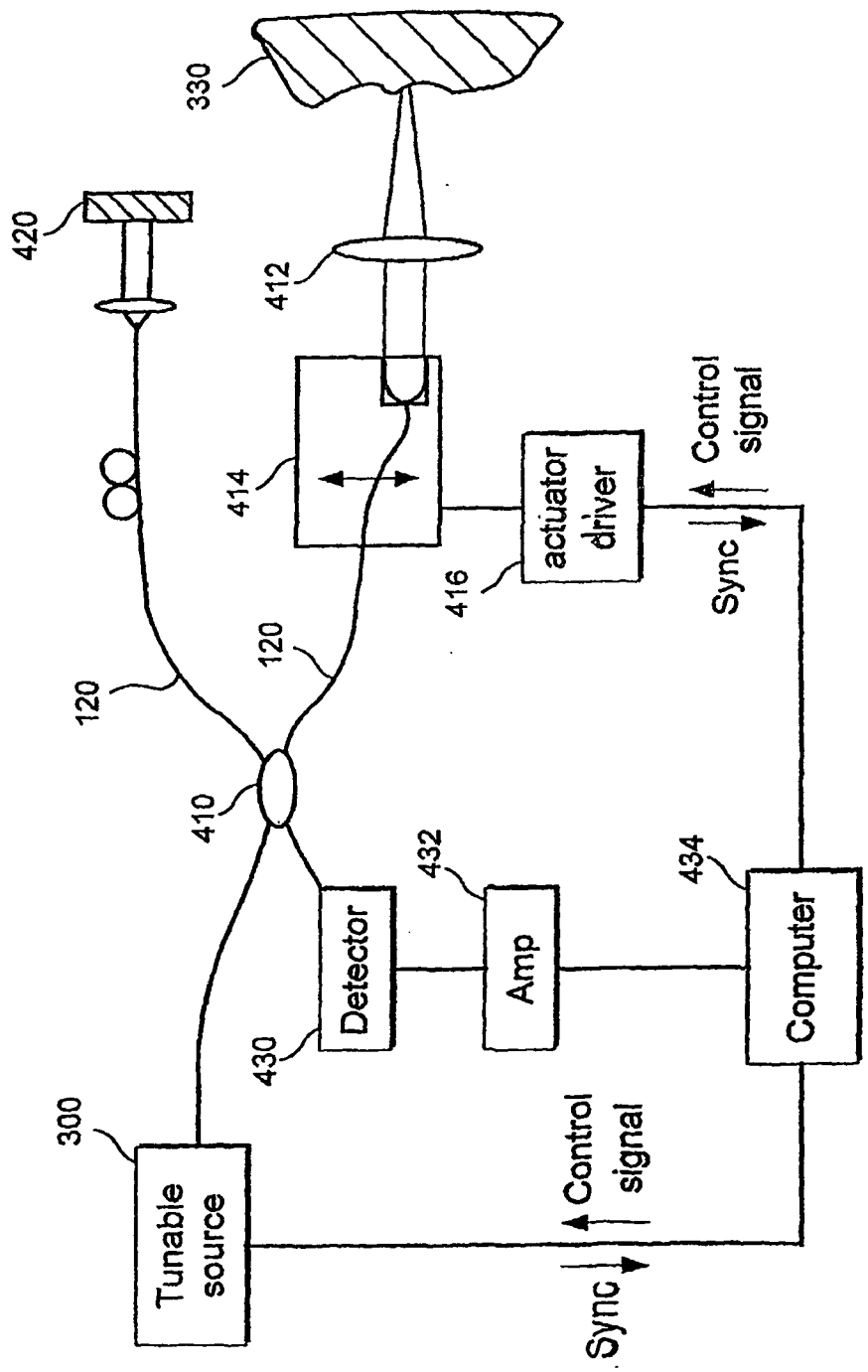
FIG. 9 is a schematic diagram of an exemplary embodiment of a frequency-domain optical coherence tomography arrangement that utilizes the tunable laser source according to the present invention.

Another exemplary application of the exemplary embodiments of the present invention is for optical coherence tomography ("OCT") the details of which are described in U.S. Pat. No. 5,956,355, the disclosure of which is incorporated herein by reference in its entirety. In one exemplary configuration, depicted in FIG. 9, an output of a tunable source 300 may be directed to a sample 330 through a fiber-optic coupler 410. An objective lens 412 in the probe may typically provide a focus near the surface or within the sample 330. The reference mirror 420 can be placed in a reference arm 120 at a position where an optical path length between two arms of the Michelson interferometer is substantially matched. Alternatively, the reference path can be configured in a transmissive, non-reflective configuration. The detector 430 may be a PIN photodiode followed by a transimpedance amplifier 432 with finite frequency bandwidth. The detector may preferably incorporate polarization diverse and dual balanced detection. The detector signal can be processed in the processor 434 through a fast Fourier transform to construct the depth image of the sample. The probe may be scanned by an actuator 414 and an actuator driver 416 to allow a 3-dimensional image of the sample to be obtained.

Figure 10B:
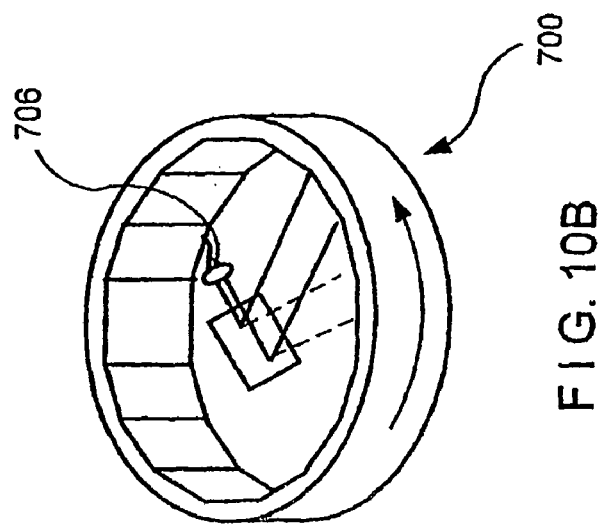
FIG. 10B is a perspective plan view of the wavelength filter shown in FIG. 10A.
Figure 10A:
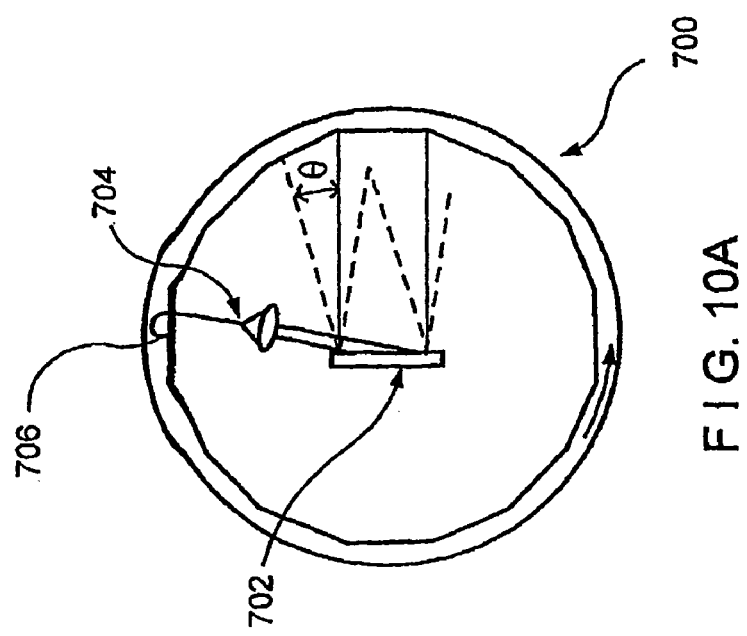
FIG. 10A is a top view of an eighth exemplary embodiment of the wavelength filter according to the present invention.

FIGS. 10A and 10B show a top and perspective view of another exemplary embodiment of the wavelength tunable filter according to the present invention. An angularly deflecting optical element 700 of this exemplary embodiment can be a rotating polygon arrangement 24 where the facets of the polygon are on the inner diameter of a hollow cylinder. A dispersing element 702 such as a diffraction grating can be placed at the center of the polygon arrangement 24. Light can be delivered to the grating through an optical fiber and collimated onto the grating so that each frequency component of the light is diffracted through a different angle (Θ). Only one narrow range of frequencies may be substantially orthogonal to one facet of the polygon arrangement 24, and therefore such frequency range may be reflected back to the diffraction grating and collected by the optical fiber 704/706. When the cylinder rotates, a surface normal direction for the illuminated polygon arrangement's facet may align with a new narrow frequency range. By rotating the cylinder, frequency tuning can thereby be achieved. When the cylinder rotation angle becomes large, an adjacent facet of the polygon arrangement 24 can become aligned with the light diffracted from the grating and the filter will repeat another frequency tuning cycle. The free spectral range and finesse can be controlled by appropriate choice of the polygon diameter, number of facets, collimated beam diameter and diffraction grating groove density.

The foregoing merely illustrates the principles of the invention. Various modifications and alterations to the described embodiments will be apparent to those skilled in the art in view of the teachings herein. For example, the invention described herein is usable with the exemplary methods, systems and apparatus described in U.S. Patent Application No. 60/514,769. It will thus be appreciated that those skilled in the art will be able to devise numerous systems, arrangements and methods which, although not explicitly shown or described herein, embody the principles of the invention and are thus within the spirit and scope of the present invention.

What is claimed is:

1. An apparatus comprising:
    a first arrangement configured to emit an electromagnetic radiation that has a spectrum whose mean frequency changes at a rate of that is greater than about 100 terahertz per millisecond, and
    a second arrangement configured to at least one of transmit or reflect at least one portion of the electromagnetic radiation based on a frequency of the electromagnetic radiation, wherein the at least one portion has a full-width-at-half-maximum frequency distribution that is smaller than about 100 GHz.

2. The apparatus according to claim 1, wherein the second arrangement is situated on or within the first arrangement.

3. The apparatus according to claim 1, wherein the mean frequency changes repeatedly at a repetition rate that is greater than about 5 kilohertz.

4. The apparatus according to claim 3, wherein the mean frequency changes over a range that is greater than about 10 terahertz.

5. The apparatus according to claim 4, wherein the spectrum has an instantaneous line width that is smaller than about 100 gigahertz.

6. The apparatus according to claim 1, further comprising a laser resonating arrangement which forms an optical circuit and which is configured to control a spatial mode of the electromagnetic radiation, wherein the first arrangement causes the electromagnetic radiation to propagate substantially unidirectionally within at least a portion of the resonating arrangement.

* * * * *